United States Patent
Takizawa et al.

(10) Patent No.: US 8,855,392 B2
(45) Date of Patent: Oct. 7, 2014

(54) MAGNETIC RESONANCE IMAGING APPARATUS AND SYNCHRONOUS MEASUREMENT METHOD

(75) Inventors: Masahiro Takizawa, Tokyo (JP); Tetsuhiko Takahashi, Tokyo (JP); Tomohiro Goto, Tokyo (JP); Takayuki Abe, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 143 days.

(21) Appl. No.: 13/389,620

(22) PCT Filed: Aug. 2, 2010

(86) PCT No.: PCT/JP2010/063001
§ 371 (c)(1),
(2), (4) Date: Feb. 9, 2012

(87) PCT Pub. No.: WO2011/018954
PCT Pub. Date: Feb. 17, 2011

(65) Prior Publication Data
US 2012/0141007 A1 Jun. 7, 2012

(30) Foreign Application Priority Data
Aug. 12, 2009 (JP) ................................. 2009-187066

(51) Int. Cl.
| | | |
|---|---|---|
| *G06K 9/00* | (2006.01) | |
| *A61B 5/055* | (2006.01) | |
| *A61B 5/00* | (2006.01) | |
| *G01R 33/567* | (2006.01) | |
| *A61B 5/0402* | (2006.01) | |
| *A61B 5/08* | (2006.01) | |
| *G01R 33/48* | (2006.01) | |
| *G01R 33/561* | (2006.01) | |

(52) U.S. Cl.
CPC .............. *A61B 5/055* (2013.01); *A61B 5/7207* (2013.01); *A61B 5/7285* (2013.01); *G01R 33/5673* (2013.01); *A61B 5/0402* (2013.01); *A61B 5/0816* (2013.01); *G01R 33/482* (2013.01); *G01R 33/4824* (2013.01); *G01R 33/5617* (2013.01)
USPC .......................................................... 382/131

(58) Field of Classification Search
CPC .................................................. G01R 33/4826
See application file for complete search history.

(56) References Cited

U.S. PATENT DOCUMENTS

2001/0038520 A1* 11/2001 Yagi .............................. 361/246
2007/0038069 A1*  2/2007 Itagaki et al. .................. 600/410

(Continued)

FOREIGN PATENT DOCUMENTS

| | | |
|---|---|---|
| CN | 1923137 A | 3/2007 |
| JP | 2005-270325 | 10/2005 |

(Continued)

OTHER PUBLICATIONS

International Search Report in PCT/JP2010/063001.

(Continued)

*Primary Examiner* — Atiba O Fitzpatrick
*Assistant Examiner* — Thomas A James
(74) *Attorney, Agent, or Firm* — Cooper & Dunham LLP

(57) ABSTRACT

An image with a desired contrast is obtained while suppressing body motion artifacts caused by both random motion and periodic motion of an object. In order to do so, an imaging sequence using a non-Cartesian sampling method is executed so as to synchronize with a biological signal only at the start time and a repetition time (TR), which is an execution interval between shots within the imaging sequence, is maintained. In addition, a time difference between a delay time and a start time of each shot is calculated, and a shot with a predetermined time difference or more is executed again after the TR time.

10 Claims, 14 Drawing Sheets

(56) References Cited

U.S. PATENT DOCUMENTS

| | | | |
|---|---|---|---|
| 2007/0249929 A1* | 10/2007 | Jeong et al. | 600/410 |
| 2008/0161678 A1 | 7/2008 | Miyazaki et al. | |
| 2008/0240536 A1* | 10/2008 | Soubelet et al. | 382/132 |
| 2009/0018433 A1* | 1/2009 | Kassai et al. | 600/413 |
| 2009/0148021 A1 | 6/2009 | Yui | |
| 2010/0141253 A1* | 6/2010 | Takizawa et al. | 324/309 |
| 2012/0302872 A1* | 11/2012 | Miyazaki et al. | 600/419 |
| 2013/0234707 A1* | 9/2013 | Miyazaki et al. | 324/309 |

FOREIGN PATENT DOCUMENTS

| | | |
|---|---|---|
| JP | 2008-119034 | 5/2008 |
| JP | 2008-295925 | 12/2008 |
| JP | 2009-160378 | 7/2009 |
| JP | 2010-179046 | 8/2010 |
| WO | WO 2007013423 A1 * | 2/2007 |

OTHER PUBLICATIONS

Liu, J., et al. (2006), "Multiple Echo 3D Hybrid Radial SSFP: Initial Applications in a Single Breath-hold Cardiac Imaging," Proc. Intl. Soc. Mag.Reson. Med. 14, p. 3376.

Oct. 9, 2013 Chinese official action (English translation thereof) in connection with corresponding Chinese patent application No. 201080035313.0.

Chinese official action dated Mar. 27, 2014 in corresponding Chinese patent application No. 2010 80 03 5313.0.

* cited by examiner

MAGNETIC RESONANCE IMAGING APPARATUS AND SYNCHRONOUS MEASUREMENT METHOD

TECHNICAL FIELD

The present invention relates to a magnetic resonance imaging (hereinafter, abbreviated as "MRI") technique for acquiring a tomographic image of an examination part of an object using a nuclear magnetic resonance (hereinafter, abbreviated as "NMR") phenomenon and in particular, to a synchronous imaging technique.

BACKGROUND ART

Generally, in the MRI, an echo signal at each grid point on the k space (space which is called a "measurement space") is collected by Cartesian sampling in which sampling parallel to the frequency encoding direction is repeated in the phase encoding direction. In Cartesian sampling, an echo signal is sampled repeatedly while changing the amount of phase encoding.

However, so-called body motion artifacts are caused in the phase encoding direction due to random body motion or periodic motion, such as the pulse, of an object. This occurs because a random phase change is added to an echo signal and this echo signal is not disposed at the correct position at the time of Fourier transform in the phase encoding direction when imaging a target whose position changes during imaging.

In order to reduce body motion artifacts due to periodic motion, there is a synchronous imaging method executed by synchronizing a repetition time (TR) of the imaging procedure, which is called an imaging sequence, with a periodic biological signal acquired from an object. As the main synchronous imaging method, there are a respiratory synchronization method which suppresses body motion artifacts caused by breathing and an electrocardiographic synchronization method which suppresses body motion artifacts caused by the movement or beating of the heart.

In the synchronous imaging method, however, the degree of freedom in setting an imaging parameter is reduced since the repetition time (TR) is restricted to the physiological period of the body. For example, when acquiring a T1-weighted image, it is preferable to set TR to about 500 msec in the MRI apparatus of 1.5 T. In the electrocardiographic synchronization method, however, TR is set in the range of 900 msec to 1 sec since it is necessary to make the sequence synchronize with an interval of the cardiac cycle of the object. Therefore, if the electrocardiographic synchronization method is used together with acquiring the T1-weighted image, it is not possible to set an optimal imaging parameter. As a result, it is difficult to acquire the correct contrast.

In order to reduce body motion artifacts regardless of whether the body motion artifacts are caused periodically or randomly, a non-Cartesian sampling method has been proposed. As examples of the non-Cartesian sampling method, a radial method (for example, refer to NPL 1), a hybrid radial method (for example, refer to NPL 2), and a spiral method (for example, refer to NPL 3) are known.

The radial method is a technique of acquiring echo signals required for reconstructing one image by performing radial sampling while changing the rotation angle with approximately one point (generally, the origin) of the measurement space as the rotation center. Since imaging is completed every rotation angle, it is difficult to cause artifacts. Moreover, since sampling is radially performed, the central portion of the measurement space is repeatedly measured. Accordingly, artifacts are less noticeable due to the addition effect. Furthermore, even when artifacts are caused, the artifacts are scattered within the image since sampling is not performed in a specific direction. Accordingly, artifacts are less noticeable compared with the Cartesian sampling method.

In addition, the hybrid radial method is realized by combining the radial method with phase encoding. In the hybrid radial method, sampling is performed by dividing the measurement space into a plurality of blades with different sampling directions and the phase encoding is performed within the blades. The hybrid radial method has not only the characteristic of the radial method but also a characteristic that it can be easily applied to the sequence of a multi-echo method which acquires a plurality of echo signals by one application of the high frequency magnetic field. In addition, an FSE method, an echo planar method, and the like are known as examples of the multi-echo method applied to the hybrid radial method.

The spiral method is a technique of acquiring echo signals required for reconstructing one image by performing spiral sampling while changing the rotation angle and the radius of rotation with approximately one point (generally, the origin) of the measurement space as the rotation center. The spiral method is applied as a high-speed imaging method since less time is wasted when filling the measurement space and the data can be efficiently collected. In addition, the spiral method is characterized in that a gradient magnetic field pulse waveform used when reading an echo signal is not a trapezoidal wave but a combination of a sine wave and a cosine wave and accordingly, the gradient magnetic field pulse waveform is efficient for the gradient magnetic field system and there is less noise when applying a gradient magnetic field.

CITATION LIST

Non Patent Literature

[NPL 1] G. H. Glover et. Al., Projection Reconstruction Techniques for Reduction of Motion Effects in MRI, Magnetic Resonance in Medicine 28: 275-289 (1992)

[NPL 2] James G. Pipe, Motion Correction With PROPELLER MRI: Application to Head Motion and Free-Breathing Cardiac Imaging, Magnetic Resonance in Medicine 42: 963-969 (1999)

[NPL 3] C. B. Ahn, High-Speed Spiral-Scan Echo planar NMR Imaging-I, IEEE Trans. Med. Imag, 1986 vol MI-5 No. 1: 1-7

SUMMARY OF INVENTION

Technical Problem

However, even if the non-Cartesian sampling method is used, the state of a part to be photographed changes greatly according to the imaging start timing in the case of imaging a part which is largely influenced by periodic motion. Accordingly, when repeating the imaging of the same part, the formed image may change for every imaging. In addition, since the size of a motion differs according to the imaging start timing, the quality of an image acquired eventually may change. The contrast of an image cannot be optimized if the non-Cartesian sampling method and the synchronous imaging method are combined in order to avoid this.

The present invention has been made in view of the above situation, and it is an object of the present invention to provide a technique for acquiring a high-quality and stable image, in which motion artifacts of an object are reduced, with a desired image contrast regardless of the part to be photographed.

Solution to Problem

In the present invention, the imaging sequence using the non-Cartesian sampling method is executed so as to synchronize with a biological signal only at the start time and executed such that the repetition time (TR) is maintained between each shot within the imaging sequence.

Specifically, there is provided a magnetic resonance imaging apparatus including: an imaging means that divides a measurement space into a plurality of regions, repeats a shot based on a non-Cartesian sampling method at repetition intervals set in advance and executes the imaging sequence in order to collect echo signals of one or more of the regions from an object; and a biological signal receiving means that receives a periodic biological signal of the object. The imaging means starts the imaging sequence after a predetermined delay time after the biological signal receiving unit receives the biological signal and repeats the imaging sequence while maintaining the repetition interval.

In addition, there is provided a synchronous measurement method in a magnetic resonance imaging apparatus including: an imaging step of repeating an imaging sequence, in which one or more echo signals corresponding to a partial region of a measurement space are collected, at predetermined repetition intervals on the basis of a non-Cartesian sampling method while changing the partial region; and a biological signal receiving step of receiving a periodic biological signal of the object. In the imaging step, the imaging sequence starts after a predetermined delay time after the biological signal is received and the imaging sequence is repeated while maintaining the repetition interval.

Advantageous Effects of Invention

According to the present invention, a high-quality and stable image, in which motion artifacts of an object are reduced, can be acquired with a desired image contrast regardless of the part to be photographed.

BRIEF DESCRIPTION OF DRAWINGS

FIG. 5(a) shows one blade and FIG. 5(b) shows the entire measurement space.

FIG. 6(a) shows a sequence example of electrocardiographic synchronization and FIG. 6(b) is an explanatory view showing a state where collected echo signals are disposed in the measurement space.

FIG. 11(a) is an explanatory view showing an example of the weighting coefficient calculation function based on the time difference, FIG. 11(b) is an explanatory view showing the position of an echo signal in one blade, and FIG. 11(c) is an explanatory view showing an example of the weighting coefficient calculation function based on the position in the measurement space.

DESCRIPTION OF EMBODIMENTS

First Embodiment

Figure 1:
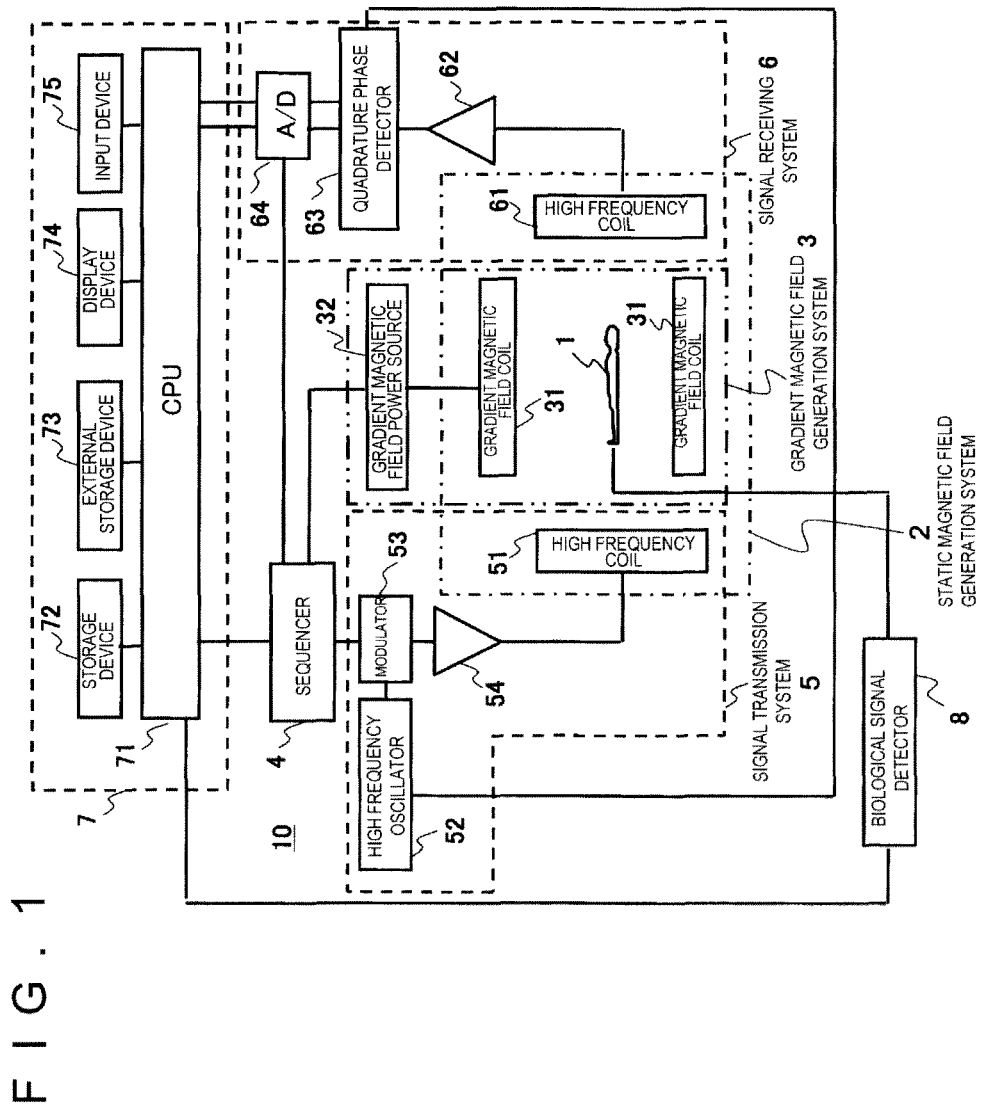
FIG. 1 is a block diagram showing the entire configuration of an MRI apparatus of a first embodiment.

Hereinafter, a first embodiment to which the present invention is applied will be described. Hereinafter, in all drawings for explaining the embodiments of the present invention, the same reference numerals are given to elements with the same functions, and repeated explanation thereof will be omitted.

First, an MRI apparatus of the present embodiment will be described. FIG. 1 is a block diagram showing the entire configuration in an example of an MRI apparatus 10 of the present embodiment. As shown in this drawing, the MRI apparatus 10 of the present embodiment acquires a tomographic image of an object 1 using an NMR phenomenon, and includes a static magnetic field generation system 2, a gradient magnetic field generation system 3, a sequencer 4, a signal transmission system 5, a signal receiving system 6, an information processing system 7, and a biological signal detector 8.

The static magnetic field generation system 2 generates a uniform static magnetic field in the space around the object 1 in the body axial direction or in a direction perpendicular to the body axis, and is formed by a permanent magnet type, normal conduction type, or superconducting type magnetic field generating means disposed around the object 1.

The gradient magnetic field generation system 3 includes gradient magnetic field coils 31 wound in three axial directions of X, Y, and Z and a gradient magnetic field power source 32 which drives each gradient magnetic field coil 31 and applies gradient magnetic field pulses, which have components in the three axial directions of X, Y, and Z, to the object 1 by driving the gradient magnetic field power source 32 of each coil according to a command from the sequencer 4, which will be described later. For example, the slice plane for the object 1 is set by applying a slice-direction gradient magnetic field pulse (Gs) in one direction of X, Y, and Z, and positional information in each direction is encoded in an echo signal by applying a phase-encoding-direction gradient magnetic field pulse (Gp) and a frequency-encoding-direction gradient magnetic field pulse (Gf) in the remaining two directions.

The signal transmission system 5 emits a high frequency magnetic field (RF) pulse in order to cause nuclear magnetic resonance in the nuclear spins of atoms which form the body tissue of the object 1, and is configured to include a high frequency oscillator 52, a modulator 53, a high frequency amplifier 54, and a transmission-side high frequency coil (transmission coil) 51. A high frequency pulse output from the high frequency oscillator 53 is amplitude-modulated by the modulator 53 at a timing based on a command from the sequencer 4, and the amplitude-modulated high frequency pulse is amplified by the high frequency amplifier 54 and is then supplied to the transmission coil 51 disposed near the object 1. As a result, the high frequency pulse is emitted to the object 1 as an RF pulse.

The signal receiving system 6 detects an NMR signal (echo signal) emitted by nuclear magnetic resonance of the nuclear spins, which form the body tissue of the object 1, and includes a receiving-side high frequency coil (receiving coil) 61, an amplifier 62, a quadrature phase detector 63, and an A/D converter 64. An echo signal of a response of the object 1 induced by the RF pulse emitted from the transmission coil 51 is detected by the receiving coil 61 disposed near the object 1 and amplified by the amplifier 62. Then, the amplified signal is divided into two signals perpendicular to each other by the quadrature phase detector 63 at a timing based on the command from the sequencer 4, and each of the divided signals is converted into a digital amount by the A/D converter 64 and transmitted to the information processing system 7 as a reception signal.

The sequencer 4 is a control means that performs the emission of an RF pulse and the application of a gradient magnetic field pulse repeatedly according to a predetermined imaging sequence, and operates under the control of the information processing system 7 and transmits various commands, which are required to collect data of a tomographic image of the object 1, to the signal transmission system 5, the gradient magnetic field generation system 3, and the signal receiving system 6.

An imaging sequence is created in advance according to the measurement purpose and is stored as a program and data in a storage device 72 or the like, which will be described later, within the information processing system 7.

The information processing system 7 performs control of the overall operation of the MRI apparatus 10, signal processing, image reconstruction processing, and the like, and includes a CPU 71, the storage device 72 such as a ROM or a RAM, an external storage device 73 such as an optical disc or a magnetic disk, a display device 74 such as a display, and an input device 75 such as a mouse, a track ball, or a keyboard. When a reception signal is input from the signal receiving system 6, the information processing system 7 performs signal processing and fills the measurement space to reconstruct an image. In addition, the reconstructed tomographic image of the object 1 is displayed on the display device 74 and is also recorded on the storage device 72 or the external storage device 73. In addition, the information processing system 7 gives a command to the sequencer 4 according to the imaging sequence stored in advance in the storage device 72 or the like. That is, these processings of the information processing system 7 are realized when the CPU 71 loads a program, which is stored in advance in the storage device 72 or the like, onto a memory and executes the program.

In addition, the imaging sequence is generated by the information processing system 7 using an imaging parameter input from an operator and a pulse sequence stored in advance, and is stored in the storage device 72 or the like.

The biological signal detector 8 includes a device attached to the object, such as an electrocardiographic sensor, a pulse wave sensor, or a respiratory sensor, and a pulse wave generator which generates a pulse wave from biological signals detected by these devices. The pulse wave generated by the pulse wave generator is transmitted to the information processing system 7. The information processing system 7 outputs an instruction according to the imaging sequence to the sequencer 4 in synchronization with the pulse wave. Moreover, in the present invention, a pulse wave acquired from the electrocardiographic sensor or the pulse wave sensor is called an electrocardiographic waveform, and a pulse wave acquired from the respiratory sensor is called a respiratory waveform.

In addition, in FIG. 1, the transmission coil 51, the receiving coil 61, and the gradient magnetic field coil 9 are provided in the static magnetic field space of the static magnetic field generation system 2 disposed in the space around the object 1. In addition, although the case where the transmission coil 51 and the receiving coil 61 are separately provided is exemplified, the present invention is not limited to this. For example, one high frequency coil may be configured to have both the functions.

The MRI apparatus 10 having the above configuration photographs the shapes or functions of the head, abdomen, limbs, and the like of the human body in a two-dimensional or three-dimensional manner by imaging the spatial distribution of the density of spin species to be photographed or the spatial distribution of excited-state relaxation. In addition, the spin species to be photographed which are widely used clinically is a proton which is a main component material of the object.

Next, the contrast of an image acquired by the MRI apparatus 10 will be described. The signal strength I of a reception signal transmitted from the signal receiving system 6 to the information processing system 7 is expressed by the following Expression (1).

[Expression 1]

$$I = k\rho \left(1 - e^{\frac{TR}{T1}}\right) e^{\frac{TE}{T2}} \qquad (1)$$

Here, k is a constant, ρ is a spin density (proton density), T1 and T2 are longitudinal relaxation time and transverse relaxation time of the tissue, TR is a repetition time of a pulse sequence, and TE is an echo time.

These relaxation times T1 and T2 are different for each tissue, and this difference becomes an image contrast. In clinical diagnosis, not only an image with a single contrast is used, but also images with a plurality of contrasts in the same part are acquired and the lesion is diagnosed in consideration of the relationship. As types of the contrast, there are T1 weighting, T2 weighting, proton density weighting, and the like.

As is apparent from Expression (1), the contrast of an image changes according to an imaging parameter set at the time of imaging, such as TR and TE. In imaging for acquiring a T1-weighted image, TE is set to be short in order to reduce the contribution of TE and TR is set to be short in order to take a difference in relaxation time by TR. For example, in a 1.5-tesla MRI apparatus, TE is set to about 10 msec and TR is set to about 500 to 600 msec. On the other hand, in imaging for acquiring a T2-weighted image, TR is set to be long in order to reduce the contribution of TR and TE is set to be long in order to take a difference in relaxation time by TE. For example, in a 1.5-tesla MRI apparatus, TE is set to about 120 msec and TR is set to about 6000 msec.

Figure 2:
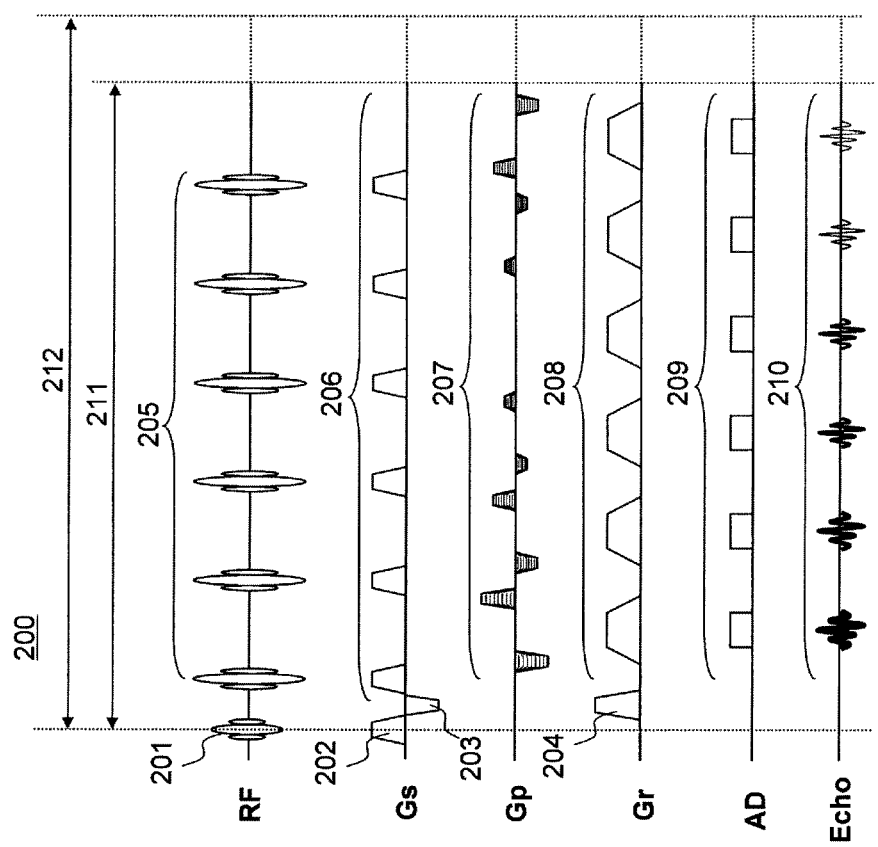
FIG. 2 is an explanatory view showing the pulse sequence of the Cartesian FSE sequence.

Next, a pulse sequence (Cartesian FSE sequence) of an FSE method to which a Cartesian sampling method is applied will be described before explaining the pulse sequence of the present embodiment. FIG. 2 is a pulse sequence diagram of a Cartesian FSE sequence 200. In this drawing, RF, Gs, Gp, Gf, AD, and Echo indicate the axes of an RF pulse, a slice gradient magnetic field, a phase encoding gradient magnetic field, a frequency encoding gradient magnetic field, A/D conversion, and an echo signal, respectively. In addition, these are the same in each pulse sequence diagram of this specification. In addition, a case of collecting six echo signal groups for each excitation RF pulse will be described as an example herein.

In the Cartesian FSE sequence 200, an excitation RF pulse 201 for giving a high frequency magnetic field to the spins within the imaging plane and a slice selection gradient magnetic field pulse 202 are applied first. A slice re-phase pulse 203 for returning the phase of the spins diffused by the slice selection gradient magnetic field pulse 202 and a frequency dephase gradient magnetic field pulse 204, which distributes the phase of the spins in advance in order to generate an echo signal, are applied immediately after application of the slice selection gradient magnetic field pulse 202. Then, a reverse RF pulse 205 for reversing the spins within the slice plane is repeatedly applied. In addition, a slice selection gradient magnetic field pulse 206 for selecting a slice, a phase encoding gradient magnetic field pulse 207, and a frequency encoding gradient magnetic field pulse 208 are applied for each application of the reverse RF pulse 205, and an echo signal 210 is collected at a timing of a sampling window 209. As described above, since the example of collecting six groups of the echo signals 210 for each excitation RF pulse 201 is illustrated herein, the reverse RF pulse 205 is applied 6 times. In addition, the echo signals 210 are generally collected as time-series signals with 128, 256, 512 or 1024 items of sampling data at the timing of each sampling window 209.

Generally, in the FSE sequence, "from application of an excitation RF pulse to collection of a predetermined number of echo signals (in the above example, six echo signals)" is called unit measurement (shot). In imaging using the Cartesian FSE sequence 200, groups of all echo signals 210 required for an image are collected at time intervals 212 by repeating a shot while changing the area of the phase encoding gradient magnetic field pulse 207 group at time intervals (TR) 211. As the number of echo signals 210 to be collected, the value of 64, 128, 256, 512, or the like per image is usually selected.

Figure 3:
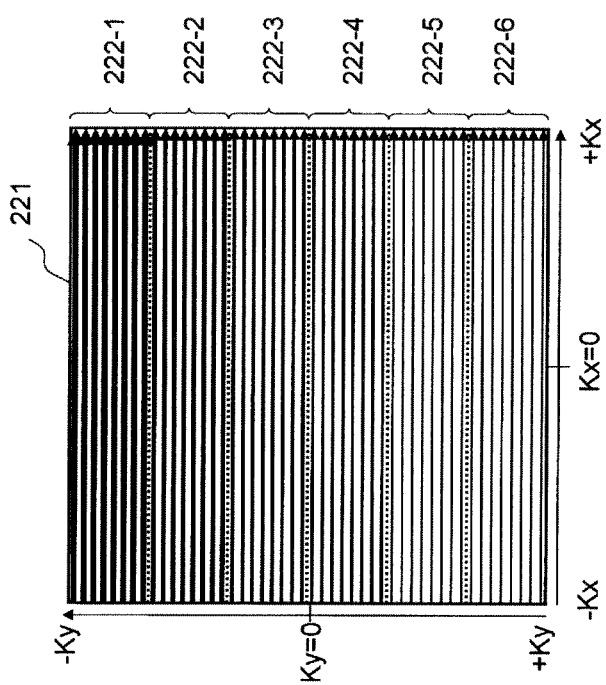
FIG. 3 is an explanatory view showing a state where echo signal groups collected by the Cartesian FSE sequence are disposed in the measurement space.

A state where groups of the echo signals 210 collected in the Cartesian FSE sequence 200 shown in FIG. 2 are disposed in a measurement space 221 is shown in FIG. 3. In this drawing, an arrow is equivalent to one echo signal 210, and the direction of the arrow indicates a scan direction of the echo signal 210. In addition, the thickness of the arrow is equivalent to the signal strength of the echo signal 210. Here, a case is illustrated in which one shot is repeated 8 times to collect a group of the echo signals 210. That is, a case of filling the measurement space 221 by the multi-shot Cartesian FSE sequence, in which a shot for collecting six groups of the echo signals 210 with one excitation RF pulse 201 is repeated 8 times, is illustrated.

In the Cartesian FSE sequence 200, a group of the phase encoding gradient magnetic field pulses 207 is controlled such that each group of the echo signals 210 is disposed in sequential order from top to bottom (that is, from −Ky to +Ky) in each block 222 by one shot. In addition, a group of the phase encoding gradient magnetic field pulses 207 is controlled such that echo signals collected at the same echo time are disposed in different lines in the same block 222 whenever the Cartesian FSE sequence 200 is repeated. A subscript of each block 222 in FIG. 3 corresponds to an echo number of the echo signal 210 in each shot which is disposed in the block 222. The echo number is given, in time order of collection, to each echo signal 210 collected in each shot of the Cartesian FSE sequence 200. That is, the larger the echo number, the longer the echo time of the echo signal. In addition, the order of filling the measurement space 221 may be changed by changing a method of changing the strength of the phase encoding gradient magnetic field pulse 207 group.

Next, a pulse sequence when a non-Cartesian sampling method is applied to the FSE method will be described. Here, a case where a hybrid radial method is applied as the non-Cartesian sampling method will be described as an example. Hereinafter, this pulse sequence is called a hybrid radial FSE sequence. Here, each block (blade) is filled with a group of echo signals acquired by one excitation.

Figure 4:
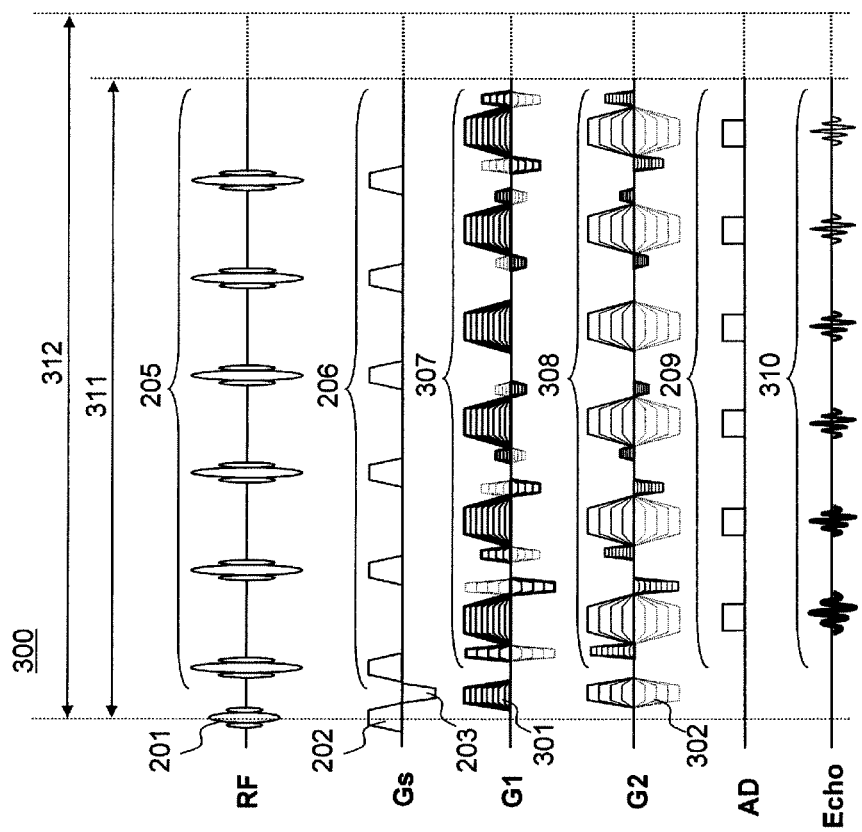
FIG. 4 is an explanatory view showing the pulse sequence of the hybrid radial FSE sequence.
Figure 5:
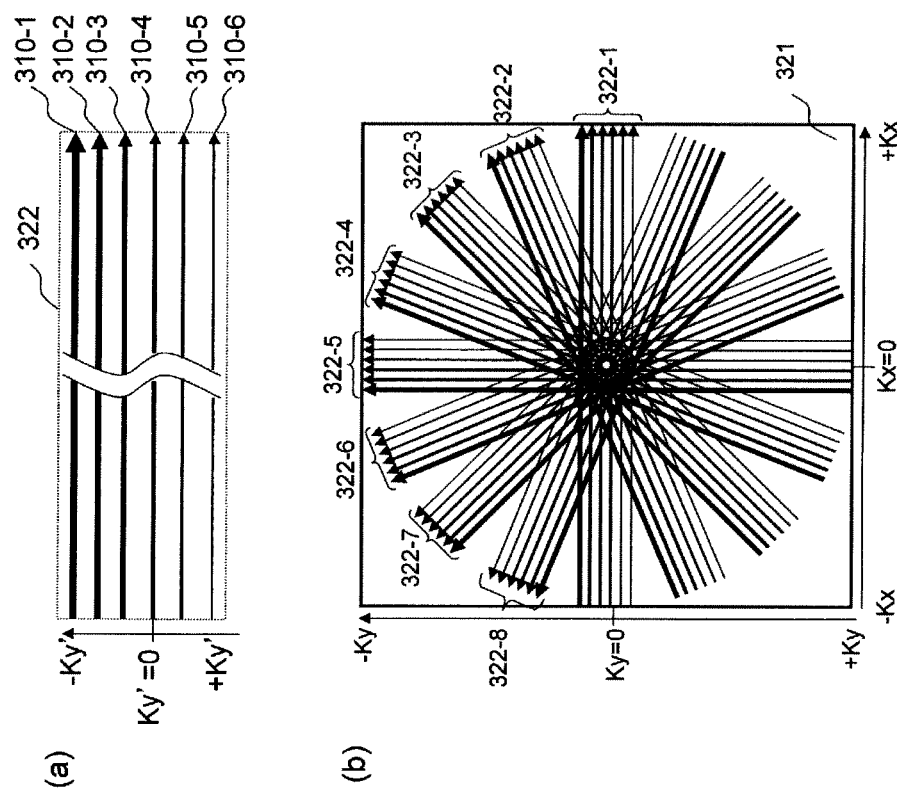
FIG. 5 is a view showing a state where echo signal groups collected by the hybrid radial FSE sequence are disposed in the measurement space, where

FIG. 4 is a pulse sequence diagram of a hybrid radial FSE sequence 300. In addition, FIG. 5 is a view showing a state where groups of echo signals collected by the hybrid radial FSE sequence 300 are disposed in a measurement space 321. The hybrid radial FSE sequence 300 is different from the Cartesian FSE sequence 200 in that there is no distinction between the phase encoding gradient magnetic field axis Gp and the frequency encoding gradient magnetic field axis Gf. In addition, these are expressed as G1 and G2 axes in FIG. 4 for the sake of convenience. In addition, a case where six echo signal groups are collected by one shot in the same manner as in the Cartesian FSE sequence 200 will be described as an example herein.

Generally, in imaging using the hybrid radial method, the measurement space is divided into a plurality of blades (unit regions) and the blades are measured at different rotation angles of the measurement space. One blade is configured to include a plurality of loci each of which corresponds to one echo signal and which are parallel to each other. Here, the rotation angle of the measurement space is an angle between a predetermined axis (in this specification, a kx axis) of the measurement space and the locus passing through the center of the measurement space in each blade. In addition, phase encoding is given to an echo signal measured in a blade.

In the hybrid radial FSE sequence 300, each blade 322 is filled with an echo signal group collected by one excitation RF pulse. Accordingly, the basic configuration of the pulse sequence for one shot is the same as that of the Cartesian FSE sequence 200.

First, the excitation RF pulse 201 for giving a high frequency magnetic field to the spins within the imaging plane and the slice selection gradient magnetic field pulse 202 are applied. The slice re-phase pulse 203 for returning the phase of the spins diffused by the slice selection gradient magnetic field pulse 202 and read dephase gradient magnetic field pulses 301 and 302, which distribute the phase of the spins in advance in order to generate an echo signal, are applied immediately after application of the slice selection gradient magnetic field pulse 202. Then, a reverse RF pulse 205 for reversing the spins within the slice plane is repeatedly applied. In addition, the slice selection gradient magnetic field pulse 206 for selecting a slice and read gradient magnetic field pulses 307 and 308 are applied for each application of the reverse RF pulse 205, and an echo signal 310 is collected at a timing of the sampling window 209. As described above, since the example of collecting six groups of the echo signals 310 for each excitation RF pulse 201 is illustrated herein, the reverse RF pulse 205 is applied 6 times.

In this case, the read dephase gradient magnetic field pulse 301 and a read gradient magnetic field pulse 307 are applied to the G1 axis, and the read dephase gradient magnetic field pulse 302 and a read gradient magnetic field pulse 308 are applied to the G2 axis. Assuming that the read direction and the phase encoding direction in the blade 322 are Kx' and Ky', respectively, the read gradient magnetic field pulses 307 and 308 are controlled such that the echo signals 310 are collected from −Ky' to Ky'. FIG. 5(a) is a view for explaining the arrangement of the echo signal 310 of one blade 322 acquired using one shot of the hybrid radial FSE sequence 300. Here, an arrow is equivalent to one echo signal 310, and the direction of the arrow indicates a scan direction of the echo signal 310. In addition, the thickness of the arrow is equivalent to the signal strength of the echo signal 310, and a subscript corresponds to an echo number. The echo number is given, in time order of collection, to each echo signal 310 collected in each shot of the hybrid radial FSE sequence 300.

Moreover, in order to measure the respective blades 322 at different rotation angles of the measurement space 321, all groups of the echo signals 310 required for an image are collected at time intervals 312 by repeatedly executing the hybrid radial FSE sequence 300 while changing the amplitudes of the read dephase gradient magnetic field pulses 301 and 302 and the read gradient magnetic field pulses 307 and 308 which are applied to two axes (G1 and G2 axes) within the slice plane at time intervals 311. By performing control in this way, each blade 322 is made to rotate radially with approximately one point of the measurement space 321 as the center.

A state where groups of the collected echo signals 310 are disposed in the measurement space 321 by repeating the hybrid radial FSE sequences 300 shown in FIG. 4 is shown in FIG. 5(b). Groups of the echo signals 310 collected in the same shot are disposed in the same blade 322. The subscript of 322 is a number (shot number) corresponding to the number of times of repetition of the FSE sequence 300 for each time interval 311. This drawing is an example when controlling the FSE sequence 300 such that half rotation is made in the counterclockwise direction and this is repeated 8 times to scan the measurement space 321. In addition, in each blade 322, an arrow is equivalent to one echo signal 310, the direction of the arrow indicates a scan direction of the echo signal 310, and the thickness of the arrow is equivalent to the signal strength of the echo signal 310. Moreover, as shown in this drawing, blades are measured at different rotation angles for each shot number.

Figure 6:
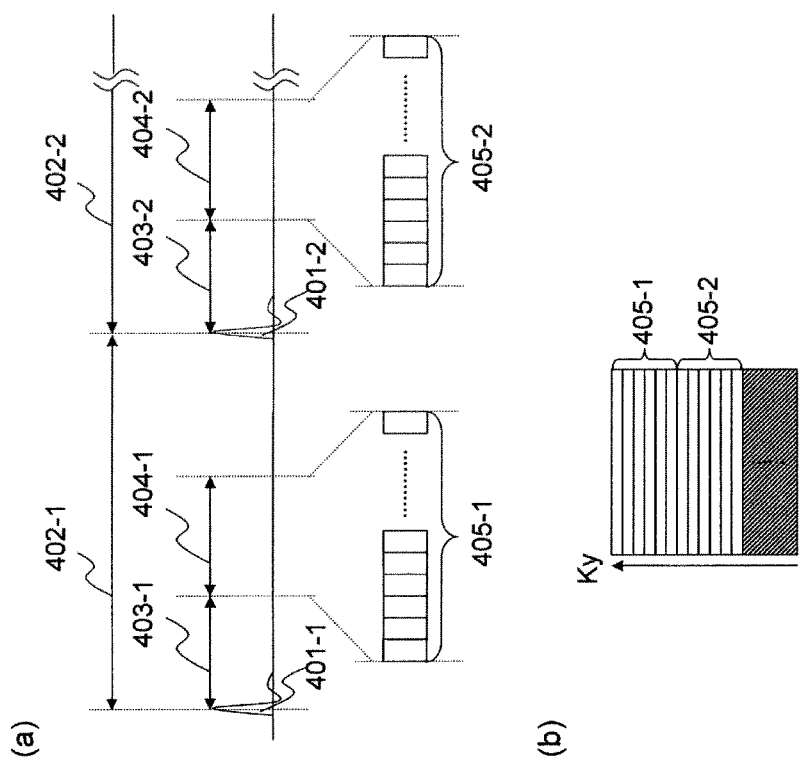
FIG. 6 is a view for explaining a synchronous imaging method, where

Next, a synchronous imaging method will be described using FIG. 6. Here, an electrocardiographic synchronization method is shown as an example.

As shown in FIG. 6(a), 401 is an electrocardiographic waveform acquired by the biological signal detector 8, and a time interval 402 is an interval between the electrocardiographic waveforms 401 (generally called an R-R interval). In the synchronous imaging method, the electrocardiographic waveform 401 is detected, and then the imaging sequence starts after a time interval 403 (hereinafter, a delay time) and an echo signal group 405 is collected within a time interval 404. After detecting each electrocardiographic waveform 401, echo signals are collected at the same timing and data required to reconstruct an image is acquired in synchronization with the electrocardiographic waveform 401. In addition, the R-R interval is also called a cardiac cycle, and the number after a hyphen indicates processing within the cardiac cycle after the n-th electrocardiographic waveform 401-n. In addition, in the following explanation, numbers after a hyphen will be omitted unless it is necessary to distinguish them in particular. In addition, although the corresponding waveform is called the electrocardiographic waveform 401 in electrocardiographic synchronization, it is generally called a biological signal 401 or a trigger signal 401.

FIG. 6(b) shows an example where the echo signal groups 405 collected in this way are disposed in a measurement space 422. Here, an example of collecting echo signals using the Cartesian sampling method is shown. A number of echo signals 405 which can be collected within the time interval 404 in each cardiac cycle are collected by changing the amount of phase encoding every echo signal 405 and are disposed in a measurement space 421. This is repeated until the entire measurement space 421 is filled. FIG. 6(b) shows an example where the measurement space 421 is filled sequentially from the top in the Ky axis direction from the echo signal 405-1 collected within the first cardiac cycle.

For example, when this electrocardiographic synchronization method is combined with the hybrid radial FSE sequence 300, generally each shot is executed within the time interval 404 in each cardiac cycle to collect the echo signal 310. Accordingly, it is necessary to match TR 311 to the R-R interval 402. However, the R-R interval is not necessarily fixed. Even if the R-R interval is approximately fixed, TR set in an image with a desired contrast does not match the R-R interval generally.

Therefore, in the present embodiment, when executing the non-Cartesian sampling method in synchronization with a biological signal, the non-Cartesian sampling method is executed in synchronization with a biological signal not every TR but in the entire imaging sequence. That is, each shot is synchronized with the electrocardiographic waveform 401 only at the start of imaging, and each subsequent shot is executed at TR intervals as normal. First, the outline of the synchronous imaging method of the present embodiment will be described using FIG. 7. Here, the electrocardiographic synchronization method will be described as an example.

Figure 7:
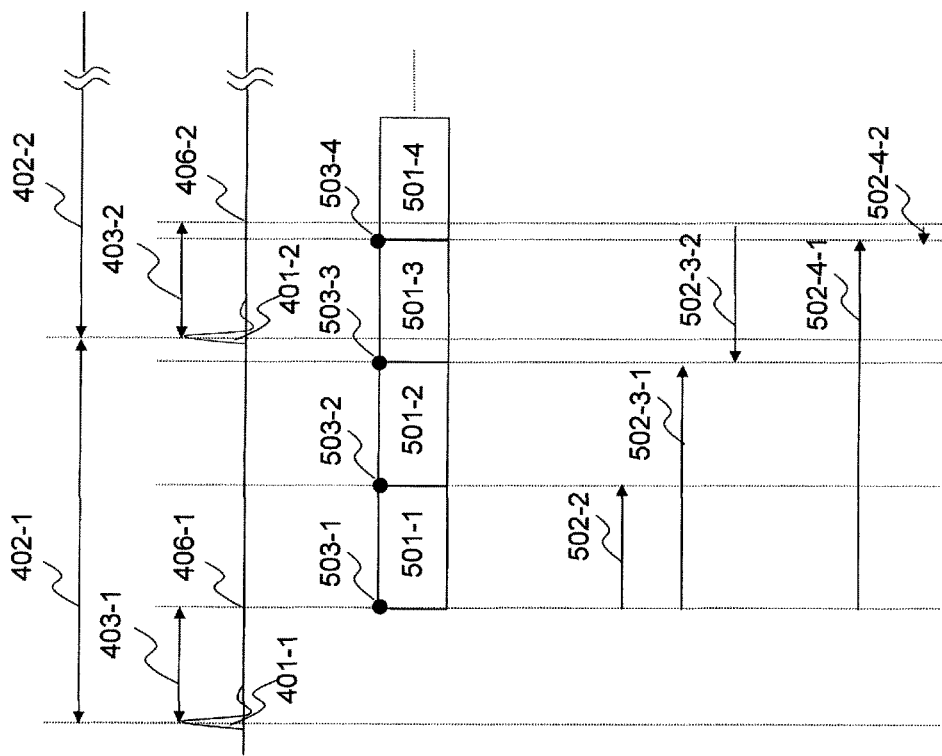
FIG. 7 is an explanatory view for describing the outline of a synchronous imaging method of the first embodiment.

In a configuration with which electrocardiographic synchronization in FIG. 7 will be described, the same number is given to the same component as in FIG. 6. In addition, assuming that the total number of shots in imaging is N (N is a natural number), 501-n (n is a natural number satisfying 1≤n≤N) indicates a shot with a shot number of n (hereinafter, an n-th shot). In addition, 502-n indicates a time difference between a shot start time 503-n of the n-th shot and a time 406 (delay time 406) after the elapse of the closest delay time 403. As shown in this drawing, in the present embodiment, only the first shot 501-1 is executed after the delay time 403 elapses set in advance from the electrocardiographic waveform 401, and the remaining shots (501-2, 501-3, . . . , 501-N) are executed at normal TR intervals.

Figure 8:
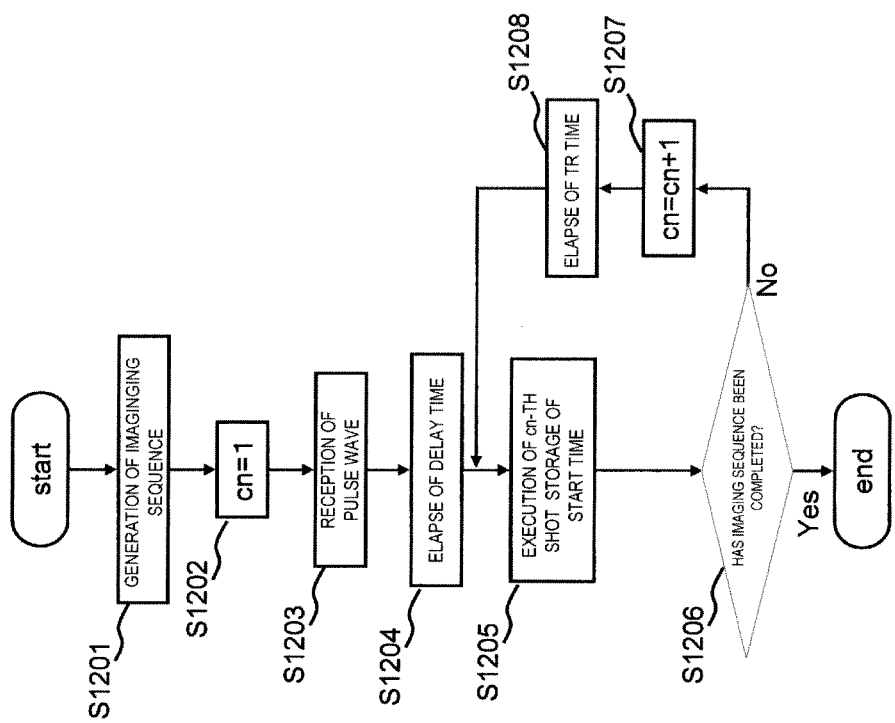
FIG. 8 is a flow chart of imaging processing of the first embodiment.

In the present embodiment, the information processing system 7 includes a synchronous imaging control unit to realize the above-described control. In addition, the information processing system 7 includes a biological signal receiving unit that receives a pulse wave from the biological signal detector 8 and notifies the synchronous imaging control unit of it independently from the control of the synchronous imaging control unit. That is, these functions of the information processing system 7 are realized when the CPU 71 loads a program, which is stored in advance in the storage device 72 or the like, onto a memory and executes the program. Hereinafter, imaging processing of the synchronous imaging control unit of the present embodiment will be described. FIG. 8 is a process flow of the imaging processing of the present embodiment.

In response to the input of an imaging parameter from an operator, the synchronous imaging control unit generates an imaging sequence (basic shape of the sequence to be executed) using a pulse sequence stored in advance (step S1201). In addition, a counter cn which counts the shot number of a shot to be executed is set to 1 (step S1202). The synchronous imaging control unit waits for reception of a pulse wave when an instruction to start is received from the operator. When a notification that a pulse wave has been received from the biological signal receiving unit is received (step S1203), the synchronous imaging control unit executes a cn-th shot according to the imaging sequence (step S1205) after the elapse of a delay time input as an imaging parameter (step S1204). In this case, the start time of the shot is stored so as to match the value of the counter cn.

After the end of the shot, the synchronous imaging control unit determines whether or not all shots set in advance have been executed, that is, whether or not the imaging sequence has been completed (step S1206). Specifically, the synchronous imaging control unit determines whether or not cn=N is satisfied assuming that the total number of shots in imaging is N. Then, the process ends when all the shots have been executed. On the other hand, when there is a shot which has not yet been executed, cn is incremented by 1 (step S1207). After the TR time elapses from the last shot start time, the process returns to step S1205 to execute the cn-th shot.

The synchronous imaging control unit of the present embodiment realizes synchronous imaging of the present embodiment by performing the imaging processing as described above, thereby filling the measurement space with echo signals. In addition, the synchronous imaging method is not limited to electrocardiographic synchronization.

In addition, the delay time 403 is set as an imaging parameter by the operator together with other imaging parameters. The optimal delay time 403 is determined by the part to be photographed and the type of a biological signal to be adopted. For example, when a biological signal is a cardiac beat, a good image can be acquired in diastole since the movement of the object 1 is generally small in diastole. Therefore, the delay time 403 is determined such that imaging starts in diastole. On the other hand, when a biological signal is breathing, the movement of the object 1 is gentle in an exhalation period and accordingly it is difficult to cause artifacts. Therefore, the delay time 403 is determined such that imaging starts in the exhalation period.

If the synchronous imaging method is not used, imaging starts at random in a body motion period of the body. For example, in the case of blood vessel imaging or the like, the state of a blood flow through a blood vessel changes in systole, during which a variation in the movement of the heart becomes largest, and diastole, during which a variation in the movement of the heart becomes smallest. For this reason, drawing of a blood vessel may change every imaging according to the start timing of the body motion period. In particular, when the repetition time TR of the imaging sequence is close to the multiple (including ½ times, ⅓ times, and the like) of the body motion period of the body, a result near the synchronous imaging is obtained in each imaging and the acquired image is close to the predetermined time phase of the body motion period. Accordingly, a difference in drawing according to the start timing appears noticeably. Therefore, drawing of a resultant image changes every imaging.

In contrast, in the present embodiment, the imaging sequence starts in synchronization with a predetermined biological signal after the delay time 403 set by the imaging parameter elapses from the trigger signal (in FIG. 7, an electrocardiographic waveform) 401. Therefore, even if a part which is largely influenced by periodic motion is repeatedly photographed, the state of a part to be photographed for periodic motion at the start of each imaging becomes approximately the same. Therefore, the influence of periodic body motion between imaging operations becomes approximately the same. For this reason, it is possible to acquire a stable image without changing the drawing of an imaging target in each imaging. On the other hand, each shot in imaging is executed at TR intervals as normal. Accordingly, a desired contrast can be acquired. In addition, since the non-Cartesian sampling method is used, body motion artifacts can be reduced.

As described above, according to the present embodiment, a fixed state can be drawn in each imaging while maintaining the advantage of the non-Cartesian sampling method capable of reducing body motion artifacts, and a desired contrast can be acquired. Therefore, a high-quality stable image can be acquired in each imaging without sacrificing the contrast regardless of a part to be photographed including a part which is easily influenced by periodic motion of the body.

In addition, although the case where the number of blocks and the number of echoes in a block in the hybrid radial method are 6 and 8 is illustrated in the above embodiment for convenience of explanation, the number of blocks and the number of echoes are limited to these. The number of blocks and the number of echoes in a block may be arbitrarily set.

Second Embodiment

Next, a second embodiment to which the present invention is applied will be described. The MRI apparatus of the present embodiment has basically the same configuration as in the first embodiment. In the first embodiment, once imaging starts, all shots are executed once in order at TR intervals thereafter. On the other hand, in the present embodiment, it is determined whether or not to adopt a result according to a time from the delay time of each shot start time, and this is repeatedly executed until the result is adopted when the result is not adopted. Hereinafter, imaging processing of the present embodiment will be described focusing on a different configuration from the first embodiment.

First, the outline of the synchronous imaging method of the present embodiment will be described. Here, similar to the first embodiment, an electrocardiographic synchronization method will be described as an example using FIG. 7. In the present embodiment, for each shot 501, a time difference 502 is calculated as an absolute value of a time between a start time 503 of the shot 501 and the closest delay time 406 after the end of the shot 501. Then, if the time difference 502 is larger than a threshold value set in advance, echo signals collected in the shot 501 are not used for image reconstruction and echo signals are collected again under the same conditions.

Here, in the calculated time difference 502, for example, in a second shot 501-2, only a trigger signal 401-1 is received at the end of the second shot 501-2. Accordingly, a time between the delay time 406-1 and the start time 503-2 is set as the time difference 502. On the other hand, in a third shot 501-3, the trigger signals 401-1 and 401-2 are received at the end of the third shot. Accordingly, it is possible to know the delay times 406-1 and 406-2. Absolute values 502-3-1 and 502-3-2 of differences between each of the delay times 406-1 and 406-2 and the start time 503-3 are calculated, and the smaller one is set as the time difference 502. Similarly for a fourth shot 501-4, differences 502-4-1 and 502-4-2 between the start time and the delay time are calculated, and the smaller one is set as the time difference 502.

As described in the first embodiment, the delay time 403 which is optimal for each part to be photographed is set as an imaging parameter. Accordingly, as a distance from the delay time 406 after the delay time 403 elapses from the trigger signal 401 increases, the corresponding part is easily influenced by periodic body motion. As a result, a state change at the time of measurement becomes large. In the present embodiment, a threshold value is set for the time difference 502 in order to prevent echo signals collected in such a state from being used for image reconstruction.

In order to realize this, in the present embodiment, the synchronous imaging control unit provided in the first embodiment further includes a time difference calculating unit, which calculates the absolute value of a time from the start time of each shot to the closest delay time as a time difference after the end of each shot, and an adoption determining unit, which determines whether or not to adopt echo signals acquired in the shot on the basis of a calculation result of the time difference calculating unit. In addition, the biological signal receiving unit includes a trigger signal storage unit which stores a time, at which a notification that a pulse wave has been received from the biological signal detector 8 is received, as a trigger reception time. That is, these functions of the information processing system 7 are realized when the CPU 71 loads a program, which is stored in advance in the storage device 72 or the like, onto a memory and executes the program.

Figure 9:
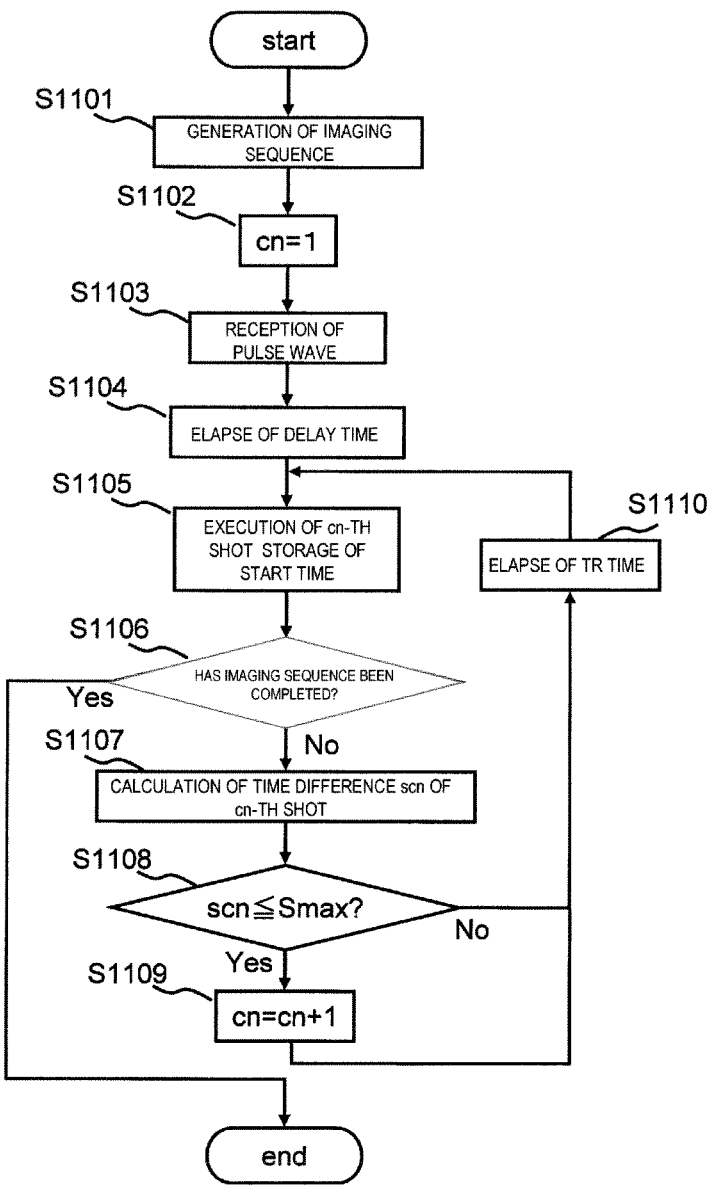
FIG. 9 is a flow chart of imaging processing of a second embodiment.

Hereinafter, imaging processing of the synchronous imaging control unit of the present embodiment will be described. FIG. 9 is a process flow of imaging processing by the synchronous imaging control unit of the present embodiment. In addition, during the following processing, the trigger signal storage unit stores the trigger reception time separately from the imaging processing whenever a pulse wave is received.

In response to the input of an imaging parameter from an operator, the synchronous imaging control unit generates an imaging sequence using a pulse sequence stored in advance (step S1101). In addition, the counter cn which counts the shot number of a shot to be executed is set to 1 (step S1102). The synchronous imaging control unit waits for reception of a pulse wave when an instruction to start is received from the operator. When a pulse wave is received (step S1103), the synchronous imaging control unit executes a cn-th shot according to the imaging sequence (step S1105) after the elapse of a delay time input as an imaging parameter (step S1104). In this case, the start time of the shot is stored so as to match the value cn of the counter.

After the end of the shot, the synchronous imaging control unit determines whether or not all shots set in advance have been executed, that is, whether or not the imaging sequence has been completed (step S1106). Specifically, the synchronous imaging control unit determines whether or not cn=N is satisfied assuming that the total number of shots in imaging is N. Then, the process ends when all the shots have been executed.

On the other hand, when there is a shot which has not yet been executed, the synchronous imaging control unit makes the time difference calculating unit calculate a time difference scn between the start time 503 of the cn-th shot and the closest delay time 406 (step S1107). Specifically, a time difference between the latest trigger reception time 401 and the delay time 406 after the elapse of the delay time 403 from the latest trigger reception time 401 (first time difference) is calculated, and a time difference between the trigger reception time 401 and the delay time 406 (second time difference) is calculated if there is a trigger reception time immediately before the latest trigger reception time. In addition, the smaller one of the first and second time differences is set as the time difference scn.

Then, the synchronous imaging control unit makes the adoption determining unit determine whether or not to adopt echo signals acquired in the shot (step S1108). That is, the synchronous imaging control unit makes the adoption determining unit determine whether or not the time difference scn is equal to or smaller than the threshold value Smax set in advance. The adoption determining unit compares scn with Smax. If scn is equal to or smaller than Smax, the adoption determining unit determines that echo signals acquired in the cn-th shot executed in step S1105 can be adopted. When it is determined that the echo signals acquired in the cn-th shot can be adopted, cn is incremented by 1 by the synchronous imaging control unit (step S1109). After the TR time elapses from the last shot start time (step S1110), the process proceeds to step S1105.

On the other hand, when the time difference scn is larger than the threshold value Smax in step S1108, the adoption determining unit determines that the echo signals acquired in the shot cannot be adopted. When it is determined that the echo signals acquired in the cn-th shot cannot be adopted, the synchronous imaging control unit waits for the elapse of the TR time from the last shot start time without incrementing Cn in order to execute the cn-th shot again (step S1110), and the process proceeds to step S1105. Then, in step S1105, when the start time matched to the value cn of the same counter is stored, it is updated to the new start time.

As described above, the synchronous imaging control unit of the present embodiment realizes synchronous imaging of the present embodiment by performing control of imaging processing, thereby filling the measurement space with echo signals determined to be adoptable.

According to the present embodiment, the TR time is maintained while using the synchronous imaging method in the imaging sequence in which the non-Cartesian sampling method is applied in the same manner as in the first embodiment. Therefore, it is possible to acquire the same effects as in the first embodiment. In addition, according to the present embodiment, when the start time of a shot is far distant from the delay time 406, the shot of the same shot number is executed again after the TR interval. Accordingly, since echo signals collected at the timing which is far distant from the delay time 406 and at which the state of the object through periodic motion is largely different are not used for image reconstruction, the quality of an image is further improved.

In addition, a value which does not lower the imaging efficiency and does not make the influence of a motion noticeable is set in advance as the value of Smax used for determination. For example, the value of Smax is set to about 1 second in the case of a respiratory synchronization method and to about several hundred milliseconds in the case of an electrocardiographic synchronization method.

Moreover, in the above-described embodiment, when it is determined that echo signals acquired in a predetermined shot (for example, an n-th shot) are not adopted, the shot (n-th shot) is executed again after the following time interval TR. However, the present invention is not limited to this. For example, all shots may be sequentially executed in order of shot numbers as in the first embodiment, and a shot (n-th shot) determined not to be adopted may be executed after all the shots are executed.

Third Embodiment

Next, a third embodiment to which the present invention is applied will be described. The MRI apparatus of the present embodiment has basically the same configuration as in the first and second embodiments. In the second embodiment, it is determined whether or not to adopt collected echo signals according to the time difference of each shot. In the present embodiment, collected echo signals are weighted according to the time difference of each shot. Hereinafter, the measurement sequence of the present embodiment will be described focusing on a different configuration from the first embodiment.

As described in the first embodiment, the delay time 403 which is optimal for each part to be photographed is selected. Accordingly, as the distance of the start time of a shot from the delay time 406 increases, that is, as the time difference 502 increases, the quality of collected echo signals is reduced. In the present embodiment, a function which decreases monotonically according to the time difference 502 is introduced as a weighting coefficient calculation function C(s), and the collected echo signals are multiplied by the acquired value as a weighting coefficient for each shot. In this way, the influence of echo signals collected in a state of the large time difference 502 on a reconstructed image is suppressed.

In order to realize this, in the present embodiment, the synchronous imaging control unit provided in the first embodiment further includes a time difference calculating unit, which calculates the absolute value of a time from the start time of each shot to the closest delay time as a time difference after the end of each shot, and a signal strength correcting unit, which corrects the signal strength by multiplying echo signals acquired in the shot on the basis of a calculation result of the time difference calculating unit by the weighting coefficient. In addition, the biological signal receiving unit includes a trigger signal storage unit which stores a time, at which a notification that a pulse wave has been received from the biological signal detector 8 is received, as a trigger reception time. That is, these functions of the information processing system 7 are realized when the CPU 71 loads a program, which is stored in advance in the storage device 72 or the like, onto a memory and executes the program. Also in the present embodiment, the trigger signal storage unit stores the trigger reception time separately whenever a pulse wave is received during the imaging processing of the synchronous imaging control unit.

Figure 10:
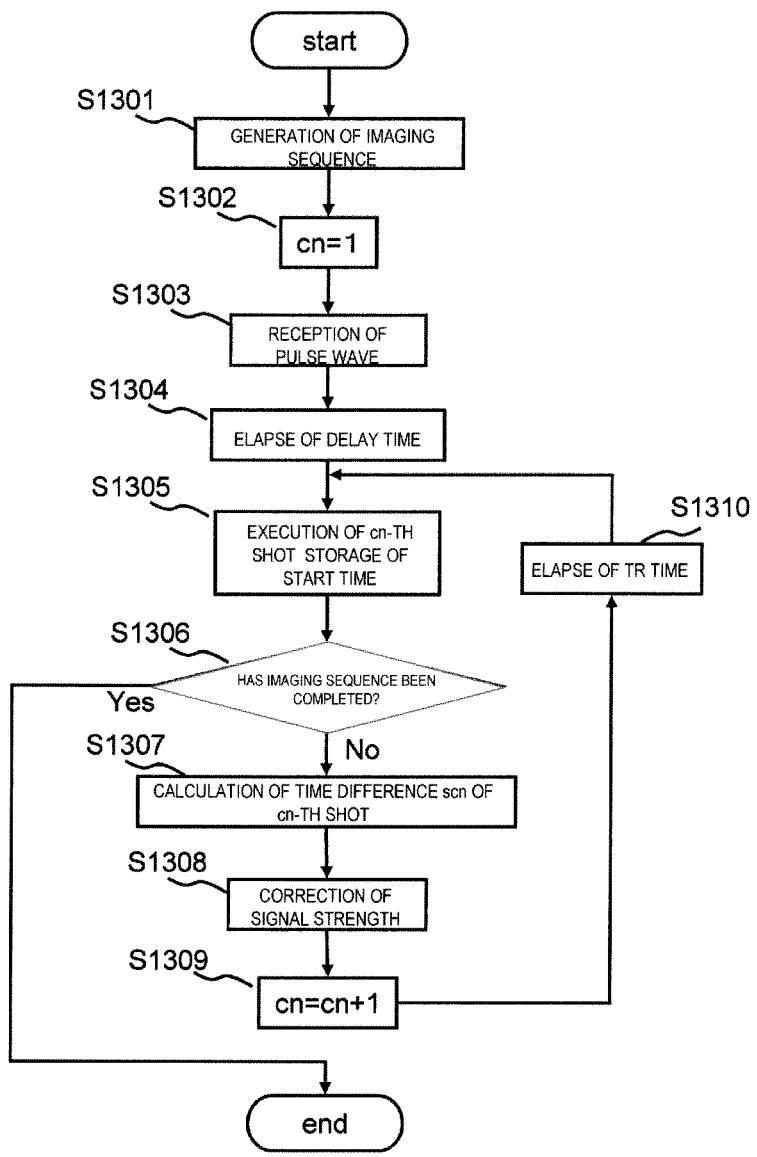
FIG. 10 is a flow chart of imaging processing of a third embodiment.

FIG. 10 is a process flow of imaging processing by the synchronous imaging control unit of the present embodiment. As shown in this drawing, the synchronous imaging control unit generates an imaging sequence using a pulse sequence, which is stored in advance, in response to the input of an imaging parameter from an operator (step S1301). In addition, the counter cn which counts the shot number of a shot to be executed is set to 1 (step S1302). The synchronous imaging control unit waits for reception of a pulse wave when an instruction to start is received from the operator. When a pulse wave is received (step S1303), the synchronous imaging control unit executes a cn-th shot according to the imaging sequence (step S1305) after the elapse of a delay time input as an imaging parameter (step S1304). In this case, the start time of the shot is stored so as to match the value cn of the counter.

After the end of the shot, the synchronous imaging control unit determines whether or not all shots set in advance have been executed, that is, whether or not the imaging sequence has been completed (step S1306). Specifically, the synchronous imaging control unit determines whether or not cn=N is satisfied assuming that the total number of shots in imaging is N. Then, the process ends when all the shots have been executed.

On the other hand, when there is a shot which has not yet been executed, the synchronous imaging control unit makes the time difference calculating unit calculate a time difference scn between the start time 503 of the cn-th shot and the closest delay time 406 (step S1307). Specifically, a time difference between the latest trigger reception time 401 and the delay time 406 after the elapse of the delay time 403 from the latest trigger reception time 401 (first time difference) is calculated, and a time difference between the trigger reception time 401 and the delay time 406 (second time difference) is calculated if there is a trigger reception time immediately before the latest trigger reception time. In addition, the smaller of the first and second time differences is set as the time difference scn.

Then, the synchronous imaging control unit makes the signal correcting unit correct the signal strength of echo signals acquired in the shot (step S1308). The correction is performed by multiplying the echo signals by the weighting coefficient C(scn) acquired from the time difference scn calculated in step S1307. After the correction, the synchronous imaging control unit increments Cn by 1 (step S1309), and the process proceeds to step S1305 after the TR time elapses from the last shot start time (step S1310).

In addition, although the signal strength of an echo signal is corrected by calculating the time difference scn for every end of a shot in the imaging processing described above, the present invention is not limited to this. For example, the time difference scn may be stored so as to match the shot number cn of each shot and be corrected before image reconstruction.

Figure 11:
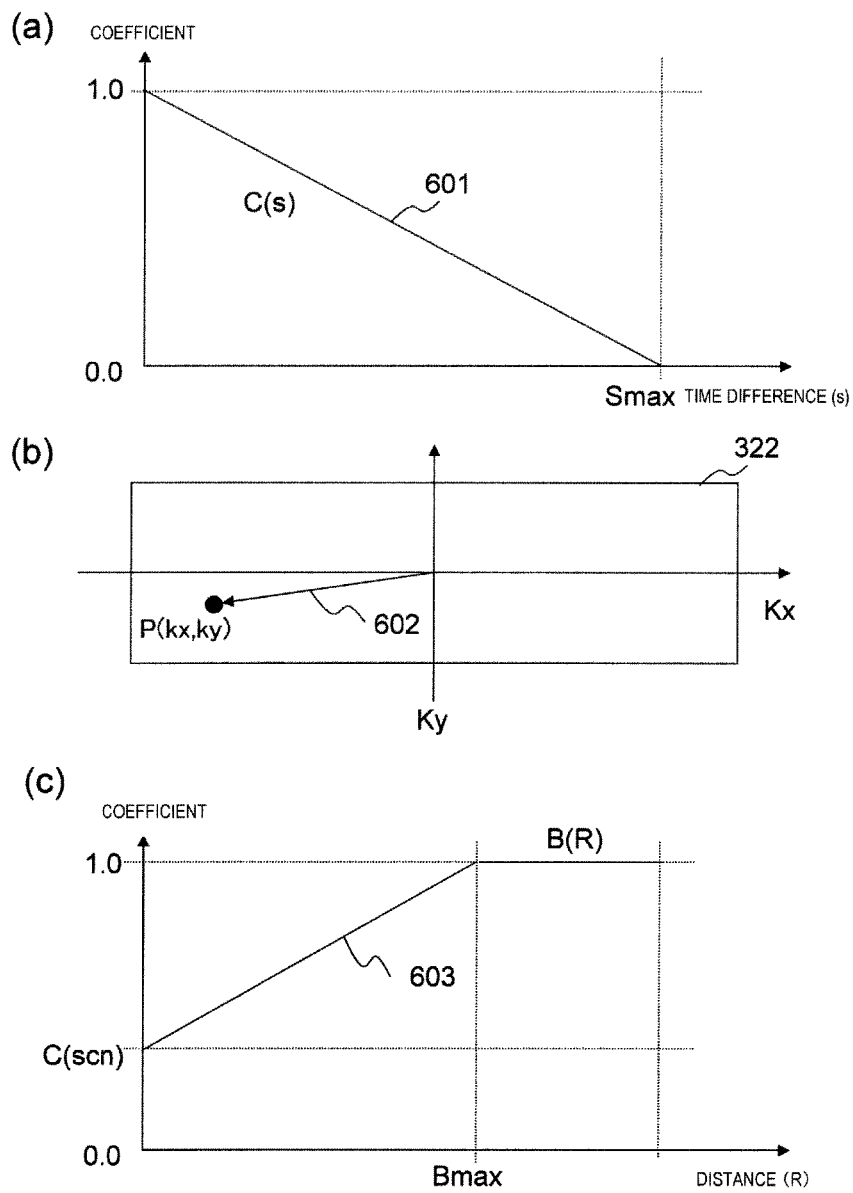
FIG. 11 is a view for explaining a weighting coefficient calculation function of the third embodiment, where

Next, an example of the weighting coefficient calculation function C(s) that the signal strength correcting unit uses will be described. FIG. 11 is an example of the weighting coefficient calculation function C(s) 601 of the present embodiment. In addition, the imaging sequence to be executed is shown in FIGS. 4 and 7. The weighting coefficient calculation function C(s) 601 shown in this drawing is 1 when the time difference s is 0, decreases linearly from 1 as the time difference s increases, and becomes 0 when the time difference s is equal to or larger than Smax. The horizontal axis in this drawing indicates the time difference 502 of each shot 501 in FIG. 7. This weighting coefficient calculation function C(s) 601 is expressed by the following Expression (2).

[Expression 2]

$$C(s) = \begin{cases} 1.0 - \dfrac{s}{S\max} & s \le S\max \\ 0.0 & S\max < s \end{cases} \quad (2)$$

In addition, the above weighting coefficient calculation function C(s) is set in advance and is stored in the storage device 72 or the like. In addition, Smax is set in the same manner as in the second embodiment.

As described above, according to the present embodiment, the signal strength correcting unit corrects the strength of an echo signal, which is acquired using a weighting coefficient calculated by the weighting coefficient calculation function C(s), according to the time difference s of each shot. For this reason, in the measurement space, the contribution of the value of an echo signal collected in a shot executed at the timing at which the time difference s is large is reduced. Therefore, according to the present embodiment, the influence of a motion can be further suppressed since an image is reconstructed from echo signals filled in the measurement space in this way. As a result, the quality of an image is further improved in addition to the effects acquired in the first embodiment.

In addition, in the embodiment described above, echo signals collected within one shot are multiplied by the same weighting coefficient. However, for example, as described in FIGS. 4 and 5, a low spatial frequency domain which is a central portion of the measurement space 321 is measured every blade 322 in the hybrid radial method. For this reason, data is excessively present in the central portion of the measurement space 321. On the other hand, there is few data in a high spatial frequency domain in which the information regarding a fine structure, such as an edge of an image, is included. In order to compensate for this, echo signals of each shot after the above-described correction may be further multiplied by the weighting coefficient according to the arrangement position of the measurement space. In this case, the weighting coefficient is determined such that the contribution becomes higher as a distance from the origin becomes larger.

FIG. 11(b) shows one blade 322 shown in FIG. 5. In the hybrid radial method, one blade 322 is a two-dimensional space specified by the phase encoding direction (Ky) and the read direction (Kx). A distance R(kx, ky) 602 from the origin of each point P(kx, ky) 804 in the blade 322 is calculated by the following Expression (3).

[Expression 3]

$$R(kx,ky)=\sqrt{kx^2+ky^2} \quad (3)$$

In the case of a blade in which echo signals acquired in the cn-th shot are disposed, the weighting coefficient is calculated from a weighting coefficient calculation function B(R) that is a monotonically increasing function which increases from the initial value C(scn) according to an increase in the distance R. An example of this weighting coefficient calculation function B(R) is shown in FIG. 11(c). The weighting coefficient calculation function B(R) 603 has a different initial value C(scn) according to each shot, decreases linearly from the initial value C(scn) according to an increase in the distance R, and becomes 1 when the distance R is equal to or larger than a predetermined value Rmax. The horizontal axis in this drawing indicates a distance R from the origin of each sampling point of an echo signal. The weighting coefficient calculation function B(R) is expressed by the following Expression (4).

[Expression 4]

$$B(R(kx, ky)) = \begin{cases} C(scn) + \dfrac{(1.0 - C(scn))(R(kx, ky))}{R\max} & R(kx, ky) \le R\max \\ 1.0 & R\max < R(kx, ky) \end{cases} \quad (4)$$

In addition, the above weighting coefficient calculation function B(R) is set in advance and is stored in the storage device 72 or the like. In addition, assuming that the number of sampling points in the read direction is Pnt, Rmax is half, for example. In addition, correction of the signal strength based on the weighting coefficient calculated from the weighting coefficient calculation function B(R) is performed after the signal strength correcting unit performs signal strength correction on the basis of the time difference s.

In this way, a weighting according to the distance R from the center is further given to each echo signal group weighted by the value of the time difference s. In this case, the weighting of the high spatial frequency domain in which the information regarding a fine structure, such as an edge of an image, is included is set to be large (here, 1.0). Thus, since an image is reconstructed from echo signals filled in the measurement space, the influence of blur can also be reduced in the image in which the influence of a motion is suppressed. As a result, the quality of an image can be further improved.

In the present embodiment which is based on the first embodiment, an example where the weighting coefficient when the time difference s exceeds the maximum Smax is set to 0.0 is shown. However, echo signals may be acquired again when the time difference s exceeds Smax by combining the technique of the present embodiment with the second embodiment. In this case, it is preferable that the synchronous imaging control unit include a signal strength correcting unit in addition to the configuration of the second embodiment.

In addition, in the present embodiment, a linear function is used as a function for calculating the weighting coefficient in FIG. 11(a). However, the weighting may be further changed according to a variable by a secondary function. Alternatively, the weighting coefficient may also be set by dividing a region by the threshold value which determines the time difference s. This is the same for the weighting coefficient according to the distance R in FIG. 11(c).

Fourth Embodiment

Next, a fourth embodiment to which the present invention is applied will be described. The MRI apparatus of the present embodiment has basically the same configuration as in the first to third embodiments. In the present embodiment, however, an imaging sequence of main imaging which performs three-dimensional measurement is used. Hereinafter, the measurement sequence of the present embodiment will be described focusing on a different configuration from each of the embodiments described above.

In the three-dimensional measurement using the non-Cartesian sampling method, not only gradient magnetic field pulses applied to the G1 and G2 axes in each shot but also the amount of application in the application axis (slice axis) direction of a slice encoding gradient magnetic field pulse is changed.

In the present embodiment, the amplitude of a slice encoding gradient magnetic field pulse is changed according to the time difference s. As described in each of the above embodiments, the delay time 403 which is optimal for each part to be photographed is selected. Accordingly, as a distance of the start time of a shot from the delay time 406 increases, that is, as the time difference 502 increases, the quality of collected echo signals is reduced. In the present embodiment, the amplitude of a slice encoding gradient magnetic field pulse is determined such that echo signals of the central portion of the measurement space in the slice direction are collected as many as echo signals collected in a shot with the small time difference 502. The amplitude is determined for each shot using a result of a function which increases monotonically according to the time difference s2 and which is introduced as a slice position fixing function Kz(s2).

In order to realize this, in the present embodiment, the synchronous imaging control unit provided in the first embodiment includes a second time difference calculating unit, which calculates a time from the latest delay time 406 to the start time 503 of the next shot as a second time difference after the end of each shot, and an amplitude determining unit, which determines the amplitude of a slice encoding gradient magnetic field pulse on the basis of a calculation result of the second time difference calculating unit. In addition, the biological signal receiving unit includes a trigger signal storage unit which stores a time, at which a notification that a pulse wave has been received from the biological signal detector 8 is received, as a trigger reception time. That is, these functions of the information processing system 7 are realized when the CPU 71 loads a program, which is stored in advance in the storage device 72 or the like, onto a memory and executes the program.

Figure 12:
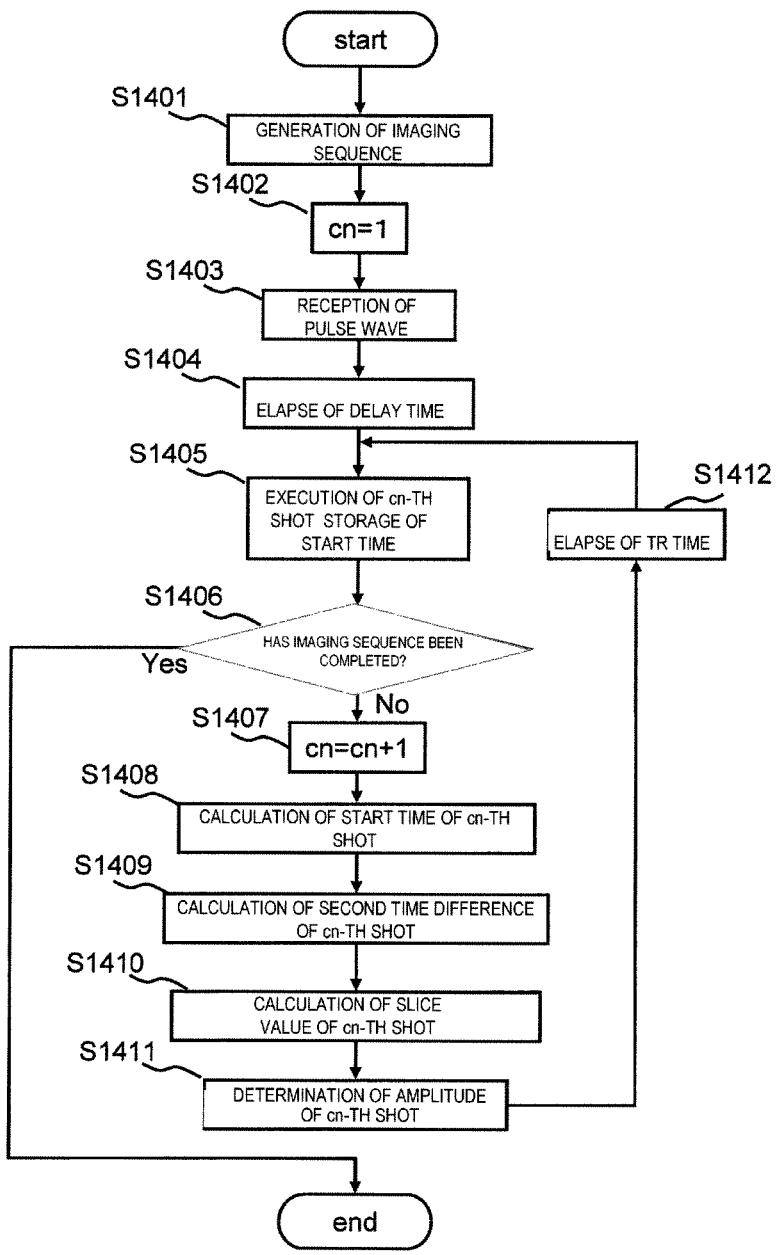
FIG. 12 is a flow chart of imaging processing of a fourth embodiment.

Hereinafter, imaging processing of the synchronous imaging control unit of the present embodiment will be described. FIG. 12 is a process flow of imaging processing by the synchronous imaging control unit of the present embodiment. In addition, during the following processing, the trigger signal storage unit stores the trigger reception time separately from the imaging processing whenever a pulse wave is received.

In response to the input of an imaging parameter from an operator, the synchronous imaging control unit generates an imaging sequence using a pulse sequence stored in advance (step S1401). In addition, the counter cn which counts the shot number of a shot to be executed is set to 1 (step S1402). The synchronous imaging control unit waits for reception of a pulse wave when an instruction to start is received from the operator. When a pulse wave is received (step S1403), the synchronous imaging control unit executes a cn-th shot according to the imaging sequence (step S1405) after the elapse of a delay time input as an imaging parameter (step S1404). In addition, since a time difference from the latest delay time is 0 in the first shot, the amplitude of a slice encoding gradient magnetic field pulse is set to 0. Moreover, in this case, the start time is (cn) of the shot is stored so as to match the value of the counter.

After the end of the shot, the synchronous imaging control unit determines whether or not all shots set in advance have been executed, that is, whether or not the imaging sequence has been completed (step S1406). Specifically, the synchronous imaging control unit determines whether or not cn=N is satisfied assuming that the total number of shots in imaging is N. Then, the process ends when all the shots have been executed. On the other hand, when there is a shot which has not yet been executed, the synchronous imaging control unit increments the counter cn by 1 (step S1407).

Then, the synchronous imaging control unit calculates a second time difference s2($cn$) of the next shot (here, the cn-th shot). Specifically, the second time difference calculating unit calculates a start time ts(cn) of the next shot first (step S1408). This is achieved by adding TR to the start time ts(cn−1) of the last shot (here, the (cn−1)-th shot). In addition, the calculated start time ts(cn) is stored so as to match the value cn of the counter. Then, the delay time 406 after the elapse of the delay time 403 from the latest trigger reception time 401 is set as the latest delay time, and this latest delay time is subtracted from the start time ts(cn) of the next shot to calculate the second time difference s2($cn$) (step S1409).

Then, the synchronous imaging control unit makes the amplitude determining unit determine the amplitude of the slice encoding gradient magnetic field pulse of the next shot (here, the cn-th shot). Here, the amplitude determining unit calculates the slice value of the slice encoding gradient magnetic field pulse of the next shot from the slice position function Kz(s2) first (step S1410). Then, the amplitude determining unit determines the amplitude, which is for acquiring the slice value, from a function A(Kz) which matches the slice value and the amplitude to each other (step S1411).

Then, the synchronous imaging control unit waits for the elapse of a TR time from the last shot start time (step S1412), and the process proceeds to step S1405 to execute the cn-th shot. In this case, the amplitude A(Kz) determined by the amplitude determining unit in step S1411 is used.

Figure 13:
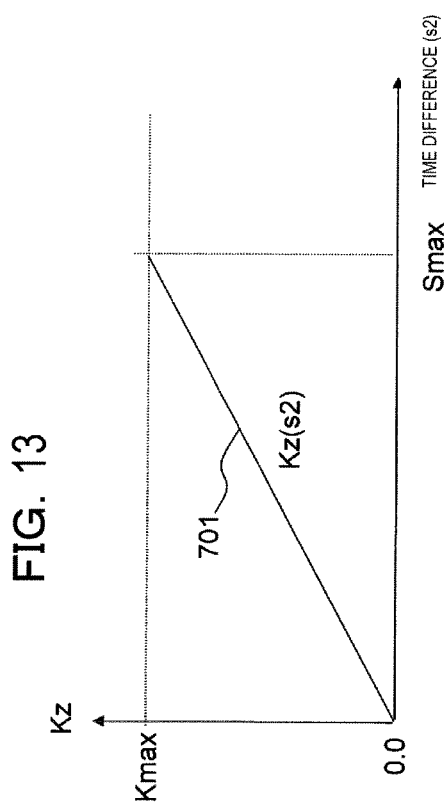
FIG. 13 is an explanatory view for describing an example of a slice value determination function of the fourth embodiment.

The synchronous imaging control unit of the present embodiment realizes synchronous imaging by performing the imaging processing in the above procedure, thereby filling the measurement space. Next, the slice position fixing function Kz(s2) used by the amplitude determining unit will be described. FIG. 13 is an example of the slice value determination function Kz(s2) 701 which determines a slice-direction position in the measurement space according to the second time difference s2. The function shown herein is a function which increases linearly from 0 according to the time difference s in the effective range (0≤s≤Smax) of the second time difference s2. The horizontal axis in this drawing indicates a second time difference when collecting echo signals of each shot 501 in FIG. 7.

After the slice value Kz(s2) is determined, the amplitude A(Kz) of a slice encoding gradient magnetic field pulse is determined so as to measure a slice of the slice value.

In addition, the slice value determination function Kz(s2) shown in FIG. 13 is expressed by the following Expression (5).

[Expression 5]

$$Kz(s2) = \begin{cases} K\max \times \dfrac{s2}{S\max} & s2 \leq S\max \\ \text{None} & S\max < s2 \end{cases} \quad (5)$$

Here, Smax is a threshold value set in advance as in each of the embodiments described above. In addition, Kmax is a value of Kz(s2) when the second time difference s2 is Smax. Thus, in the slice value determination function Kz(s2) of the present embodiment, echo signals acquired in the corresponding shot are not used for image reconstruction when the second time difference s2 exceeds Smax.

In addition, this slice value determination function Kz(s) is set in advance and is stored in the storage device 72 or the like. In addition, Kz(s2) calculated by Expression (5) is only a positive value but is the same in the measurement space. Accordingly, any value of Kz(s2) and −Kz(s2) may also be used. In addition, when Kz(s2) is acquired first and then the same second time difference s2 is acquired, −Kz(s2) may be used. In addition, positive and negative values may be alternately assigned to shots.

As described above, according to the present embodiment, the amplitude of the slice encoding gradient magnetic field is determined according to the second time difference from the delay time. As a result, echo signals with higher quality can be disposed in the low spatial frequency domain of the measurement space in the slice direction. Therefore, even in the three-dimensional measurement, a high-quality and stable image can be acquired with a desired contrast in the same manner as in the first embodiment.

Figure 14:
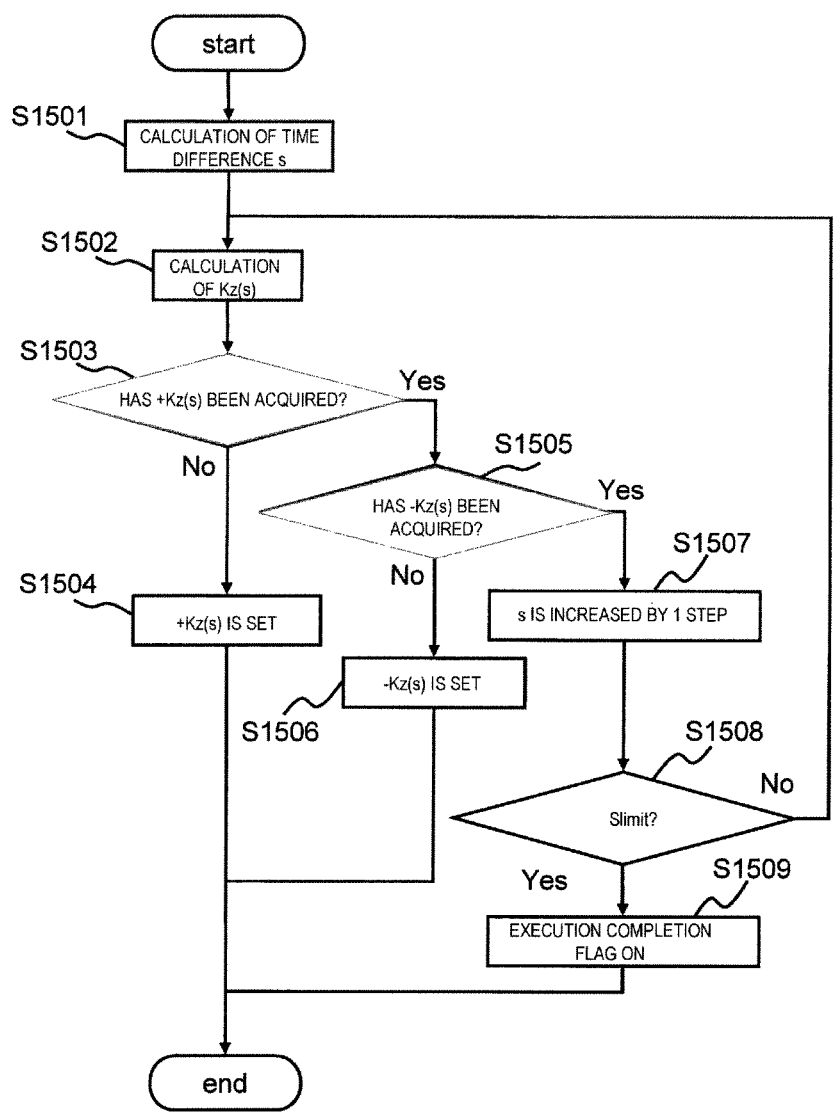
FIG. 14 is a flow chart of amplitude determination processing of the fourth embodiment.

In addition, according to the method of the present embodiment, the same slice value Kz(s2) can be acquired if corresponding shots have the same second time difference s2. Therefore, the same slice value Kz(s2) may be repeatedly acquired. The amplitude determining unit may be configured to determine the amplitude in consideration of such a case. Amplitude determination processing in this case will be described using FIG. 14. In addition, the amplitude determination processing is a processing of steps S1408 to S1411 in the above-described process. Here, the slice value Kz(s2) corresponding to each amplitude A(Kz), which has been determined and measured, is stored as an executed slice value.

The second time difference s2 is calculated in the method of steps S1408 and S1409 described above (step S1501). Here, the calculated second time difference s2 is set to s2$cn$. Then, the slice value Kz(s2$cn$) is calculated by the slice value determination function Kz(s2) (step S1502). It is determined whether or not a slice of the calculated slice value Kz(s2$cn$) has been acquired (step S1503). Such determination is performed on the basis of whether or not Kz(s2cn) calculated as the executed slice value is stored. If Kz(s2cn) is stored, it is determined that the execution has been completed.

If the slice value Kz(s2cn) has not yet been executed, the calculated amplitude Kz(s2cn) is stored as the executed slice value and the amplitude A(Kz) corresponding to Kz(s2cn) is determined as an amplitude (step S1504). Then, the amplitude determination processing ends. On the other hand, if the slice value Kz(s2cn) has been executed, it is determined whether or not a slice of −Kz(s2cn) which is a negative value of the calculated amplitude Kz(s2cn) has been acquired (step S1505). If the slice value Kz(s2cn) has not yet been executed, −Kz(s2cn) is stored as the executed slice value and the corresponding amplitude A(Kz) is determined as an amplitude (step S1506). Then, the amplitude determination processing ends.

If −Kz(s2cn) has also been executed, the value s2cn acquired as the second time difference s2 is increased by Δs expressed by the following Expression (6) (s2cn=s2cn+Δs) (step S1407).

[Expression 6]

$$\Delta s = \frac{K\max}{S\max} \quad (6)$$

Then, it is determined whether or not the second time difference s2cn after the increase exceeds a threshold value Slimit set in advance (step S1408). When the second time difference s2cn after the increase does not exceed the threshold value Slimit, the process returns to step S1402 to continue the processing. When the second time difference s2cn after the increase exceeds the threshold value Slimit, A(s) corresponding to the original Kz(s) is set as the amplitude and is also output together with a flag indicating that the execution has already been completed, and the amplitude determination processing ends.

In addition, Slimit is set such that imaging efficiency is not reduced and the influence of a motion is not noticeable. For example, Slimit may be a function of the second time difference s2. In this case, when the second time difference s2 is small, Slimit is set to be large in order to increase the possibility of slice acquisition since the quality of an acquired echo signal is high. When the second time difference s2 is large, Slimit is set to be small in order to narrow the acquisition slice range.

In addition, when the amplitude is determined together with a flag indicating that the execution has already been completed in this amplitude determination processing, synchronous imaging control unit executes the imaging sequence but does not collect echo signals. Alternatively, the synchronous imaging unit executes the imaging sequence to collect echo signals but does not use these echo signals for image reconstruction.

By configuring the amplitude determination processing in this way, it is possible to avoid repetition of echo signal collection at the same amplitude. In addition, even if it is not necessary to acquire echo signals, the contrast of an image can be maintained by executing the sequence while maintaining the repetition time.

Moreover, in the present embodiment described above, the case where the imaging processing of the first embodiment is used has been described as an example of imaging processing other than the slice direction. However, it may also be the imaging processing of the second or third embodiment. In addition, the weighting coefficient may be applied to an echo signal in the slice direction as in the third embodiment. By applying the weighting coefficient also in the slice direction, the quality of an image is further improved.

In addition, although two-dimensional measurement has been described as an example in the first to third embodiments, three-dimensional measurement may be adopted.

In addition, although the case using the hybrid radial sampling method as the non-Cartesian sampling method has been described as an example in the above embodiments, the non-Cartesian sampling method is not limited to this. For example, a radial sampling method may be used. In addition, a spiral method of sampling the measurement space spirally may be used.

The above is a specific embodiment to which the present invention is applied. However, the present invention is not limited to the content disclosed in each of the embodiments described above, and various embodiments based on the spirit of the present invention may be adopted.

REFERENCE SIGNS LIST

1: object
2: static magnetic field generation system
3: gradient magnetic field generation system
4: sequencer
5: signal transmission system
6: signal receiving system
7: information processing system
8: biological signal detector
10: MRI apparatus
31: gradient magnetic field coil
32: gradient magnetic field power source
51: transmission coil
52: high frequency oscillator
53: modulator
54: high frequency amplifier
61: receiving coil
62: amplifier
63: quadrature phase detector
64: A/D converter
71: CPU
72: storage device
73: external storage device
74: display device
75: input device
200: Cartesian FSE sequence
201: excitation RF pulse
202: slice selection gradient magnetic field pulse
203: slice re-phase pulse
204: frequency dephase gradient magnetic field pulse
205: reverse RF pulse
206: slice selection gradient magnetic field pulse
207: phase encoding gradient magnetic field pulse
208: frequency encoding gradient magnetic field pulse
209: sampling window
210: echo signal
211: time interval (TR)
212: time interval
221: measurement space
222: block
300: hybrid radial FSE sequence
301: read dephase gradient magnetic field pulse
302: read dephase gradient magnetic field pulse
307: read gradient magnetic field pulse
308: read gradient magnetic field pulse
310: echo signal 311: time interval
312: time interval
321: measurement space
322: blade
401: electrocardiographic waveform
402: R-R time
403: delay time
404: time interval
405: echo signal group
406: delay time
421: measurement space
501: shot
502: time difference
503: shot start time
601: weighting coefficient calculation function
602: distance R from origin
603: weighting coefficient calculation function
701: slice value determination function

The invention claimed is:

1. A magnetic resonance imaging apparatus comprising:
an imaging control unit that repeats an imaging sequence, in which one or more echo signals corresponding to a partial region of a measurement space are collected, at predetermined repetition time (TR) intervals on the basis of a non-Cartesian sampling method while changing the partial region; and
a biological signal receiving unit that receives a plurality of periodic biological signals of an object,
wherein based on one biological signal amongst the plurality of periodic biological signals received by the biological signal receiving unit the imaging control unit starts and repeats the imaging sequence at the same repetition time (TR) intervals after a predetermined delay time from the one biological signal,
wherein the biological signal receiving unit includes a biological signal receiving time storage unit which stores a corresponding receiving time as a biological signal receiving time whenever a biological signal is received while the imaging control unit is executing the imaging sequence, and
the imaging control unit includes a time difference calculating unit which calculates a minimum value of a time between a start time of a corresponding shot and a delay time after elapse of the delay time from each biological signal receiving time, as a time difference, in each shot and an adoption determining unit which determines that an echo signal collected in a corresponding shot is not adopted when the time difference exceeds a threshold value set in advance, and executes again the shot determined not to be adopted by the adoption determining unit after the repetition time elapses from the start of the shot.

2. A magnetic resonance imaging apparatus comprising:
an imaging control unit that repeats a shot using an imaging sequence, in which one or more echo signals corresponding to a partial region of a measurement space are collected, at predetermined repetition intervals on the basis of a non-Cartesian sampling method while changing the partial region; and
a biological signal receiving unit that receives a periodic biological signal of an object,
wherein the imaging control unit starts the imaging sequence after a predetermined delay time after the biological signal receiving unit receives the biological signal and repeats the imaging sequence while maintaining the repetition interval, and
wherein the biological signal receiving unit includes a biological signal receiving time storage unit which stores a corresponding receiving time as a biological signal receiving time whenever a biological signal is received while the imaging control unit is executing the imaging sequence, and
the imaging control unit includes a time difference calculating unit which calculates a minimum value of a time between a start time of a corresponding shot and a delay time after elapse of the delay time from each biological signal receiving time, as a time difference, in each shot and a signal strength correcting unit which acquires a corrected echo signal by multiplying an echo signal collected in the shot by a weighting coefficient which decreases as the time difference increases.

3. The magnetic resonance imaging apparatus according to claim 1,
wherein the imaging control unit further includes a signal strength correcting unit, which acquires a corrected echo signal by multiplying an echo signal collected in the shot by a weighting coefficient which decreases as the time difference increases.

4. The magnetic resonance imaging apparatus according to claim 2,
wherein the aging control unit further includes a second signal strength correcting unit which multiplies the corrected echo signal by a second weighting coefficient which increases as a distance from an origin in the measurement space of the echo signal increases.

5. A magnetic resonance imaging apparatus comprising:
an imaging control unit that repeats a shot using an imaging sequence, in which one or more echo signals corresponding to a partial region of a measurement space are collected, at predetermined repetition intervals on the basis of a non-Cartesian sampling method while changing the partial region; and
a biological signal receiving unit that receives a periodic biological signal of an object,
wherein the imaging control unit starts the imaging sequence after a predetermined delay time after the biological signal receiving unit receives the biological signal and repeats the imaging sequence while maintaining the repetition interval, and
wherein the imaging sequence is for measuring a three-dimensional measurement space including a slice encoding gradient magnetic field,
the biological signal receiving unit includes a biological signal receiving time storage unit which stores a corresponding receiving time as a biological signal receiving time whenever a biological signal is received while the imaging control unit is executing the imaging sequence, and
the imaging control unit further includes a second time difference calculating unit which calculates a time between a time after elapse of the delay time from a latest biological signal receiving time and a start time of a corresponding shot, as a second time difference, in each shot and an amplitude control unit which determines an amplitude of the slice encoding gradient magnetic field pulse such that an echo signal collected in a shot with the smaller second time difference is disposed at a position closer to a central portion of the measurement space in a slice direction.

6. The magnetic resonance imaging apparatus according to claim 1, wherein the imaging sequence is for measuring a three-dimensional measurement space including a slice encoding gradient magnetic field, and the imaging control unit further includes a second time difference calculating unit which calculates a time between a time after elapse of the delay time from a latest biological signal receiving time and a start time of a corresponding shot, as a second time difference, in each shot and an amplitude control unit which determines an amplitude of the slice gradient magnetic field pulse such that an echo signal collected in a shot with the smaller second time difference is disposed at a position closer to a central portion of the measurement space in a slice direction.

7. A synchronous measurement method in a magnetic resonance imaging apparatus comprising:

an imaging step of repeating an imaging sequence, in which one or more echo signals corresponding to a partial region of a measurement space are collected, at predetermined repetition time (TR) the basis of a non-Cartesian sampling method while changing the partial region; and a biological signal receiving step of receiving a plurality of periodic biological signals of an object, wherein in the imaging step and based on one biological signal amongst the plurality of periodic biological signals received in the biological signal receiving step, the imaging sequence starts and is repeated at the same repetition time (TR) intervals after a predetermined delay time from the one biological signal, wherein based on only the one biological signal amongst the plurality of periodic biological signals received by the biological signal receiving step, the imaging starts and repeats the imaging sequence at the same repetition time (TR) intervals, with no time interval between adjacent two repetitions of the imaging sequence after a predetermined delay time from the one biological signal.

8. A magnetic resonance imaging apparatus comprising:

an imaging control unit that repeats an imaging sequence, in which one or more echo signals corresponding to a partial region of a measurement space are collected at predetermined repetition time (TR) intervals on the basis of a non-Cartesian sampling method while changing the partial region; and a biological signal receiving unit that receives a plurality of periodic biological signals of an object, wherein based on one biological signal amongst the plurality of periodic biological signals received by the biological signal receiving unit the imaging control unit starts and repeats the imaging sequence at the same repetition time (TR) intervals after a predetermined delay time from the one biological signal, wherein based on only the one biological signal amongst the plurality of periodic biological signals received by the biological signal receiving unit, the imaging control unit starts and repeats the imaging sequence at the same repetition time (TR) intervals, with no time interval between adjacent two repetitions of the imaging sequence, after a predetermined delay time from the one biological signal.

9. The magnetic resonance imaging apparatus according to claim 8, wherein the partial region is a blade including a plurality of trajectories which are parallel to each other and each of which corresponds to one echo signal, and the imaging control unit measures one or more echo signals corresponding to one blade by one imaging sequence and repeats the imaging sequence while changing an angle of the blade with respect to a predetermined axis of the measurement space.

10. The magnetic resonance imaging apparatus according to claim 9, wherein the imaging sequence is based on an FSE sequence.

* * * * *